United States Patent [19]
Thomson et al.

[11] Patent Number: 6,133,313
[45] Date of Patent: Oct. 17, 2000

[54] INSECTICIDAL AVOCADOFURANS AND TRIOLEIN

[75] Inventors: William W. Thomson; Kathryn A. Platt; John T. Trumble, all of Riverside, Calif.; Cesar Rodriguez-Saona, Lima, Peru

[73] Assignee: The Regents of the University of California, Oakland, Calif.

[21] Appl. No.: 09/070,440

[22] Filed: Apr. 30, 1998

Related U.S. Application Data

[60] Provisional application No. 60/083,333, Apr. 27, 1998.
[51] Int. Cl.⁷ .................................................. A61K 31/34
[52] U.S. Cl. ........................................... 514/461; 549/506
[58] Field of Search .............................. 549/506; 514/461

[56] References Cited

U.S. PATENT DOCUMENTS 5,468,490  11/1995  Huber et al. ........................ 424/78.03

OTHER PUBLICATIONS

Chem Abstr vol. 122, Abstr. No. 26400. Farines et al, J Am Oil Chem. Soc. 72(4), p. 473–476, 1995.

Chem. Abstr. vol. 120, Abstr. No. 158810. Spreng et al, Flavour Fragrance J. 8(4) p. 201–207(1993), 1994.

Neeman et al, Applied Microbiology, vol. 19(3), p. 470–473, 1970.

*Primary Examiner*—Bernard Dentz
*Attorney, Agent, or Firm*—Hana Verny

[57] ABSTRACT

Novel insecticidal compounds, specifically avocadofurans and triolein, isolated from specialized idioblast cells of the avocado. Avocadofurans, 2-(tetradecyl)furan, 2-(pentadecyl)furan, 2-(hexadecyl)furan, 2-(heptadecyl)furan, 2-(octadecyl)furan, 2-(1E-pentadecenyl)furan, 2-(1Z-pentadecenyl)furan, 2-(8Z,11Z-heptadecadienyl)furan, and the triglyceride triolein possessing an insecticidal activity inhibiting larval growth. Insecticidal formulations suitable for control of *S. exigua* pest.

21 Claims, 13 Drawing Sheets

FIG. 1
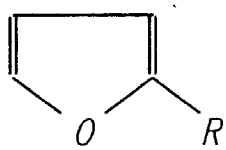
1: R = $C_{15}H_{31}$
2: R = 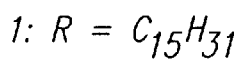 $C_{13}H_{27}$
3: R = 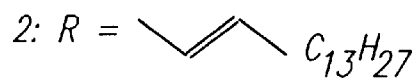 $C_{13}H_{27}$
4: R = $C_{17}H_{35}$
5: R = 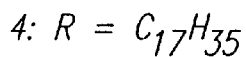 $C_{15}H_{31}$
6: R = $(CH_2)_7CH=CHCH_2CH=CH(CH_2)_4CH_3$
7: R = $CH=CH(CH_2)_5CH=CHCH_2CH=CH(CH_2)_4CH_3$
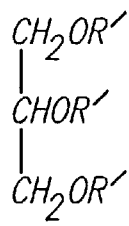
8: R′ = $C(O)(CH_2)_7CH=CH(CH_2)_7CH_3$

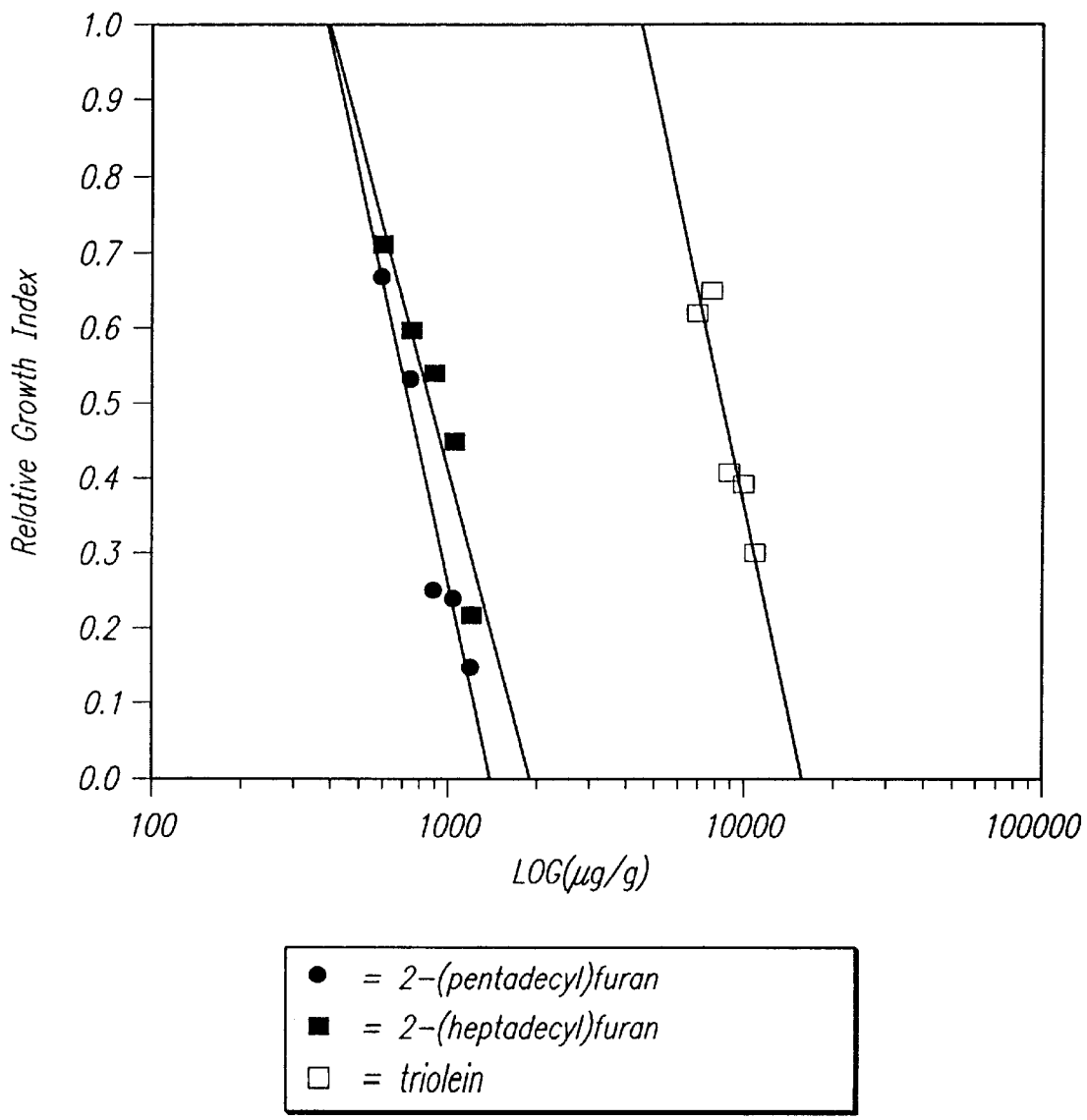

1 = 2-(Tetradecyl)furan
2 = 2-(Hexadecyl)furan
3 = 2-(Octadecyl)furan
4 = 2-(Pentadecyl)furan
5 = 2-(Heptadecyl)furan
6 = Control ☐ 2-(PENTADECYL)FURAN TREATMENT (μmoles/g)
☐ 2-(HEPTADECYL)FURAN TREATMENT (μmoles/g)

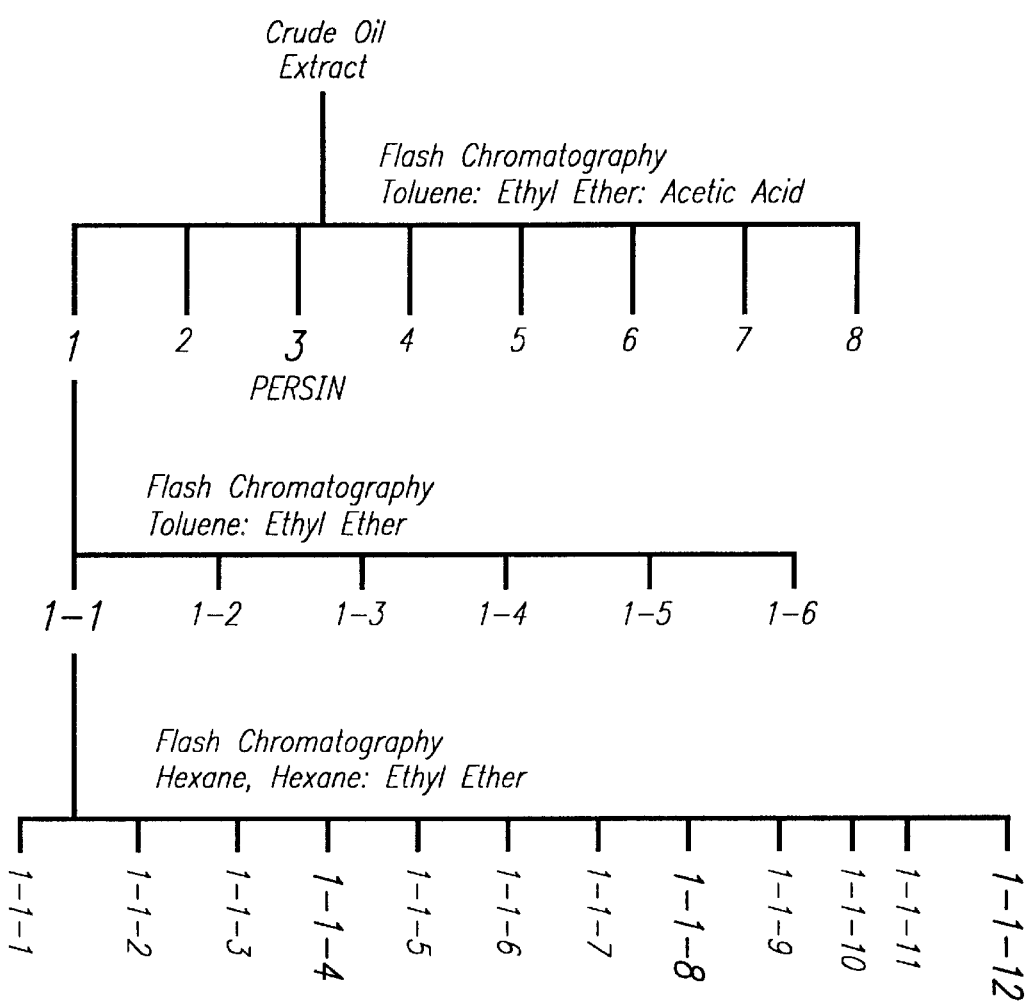

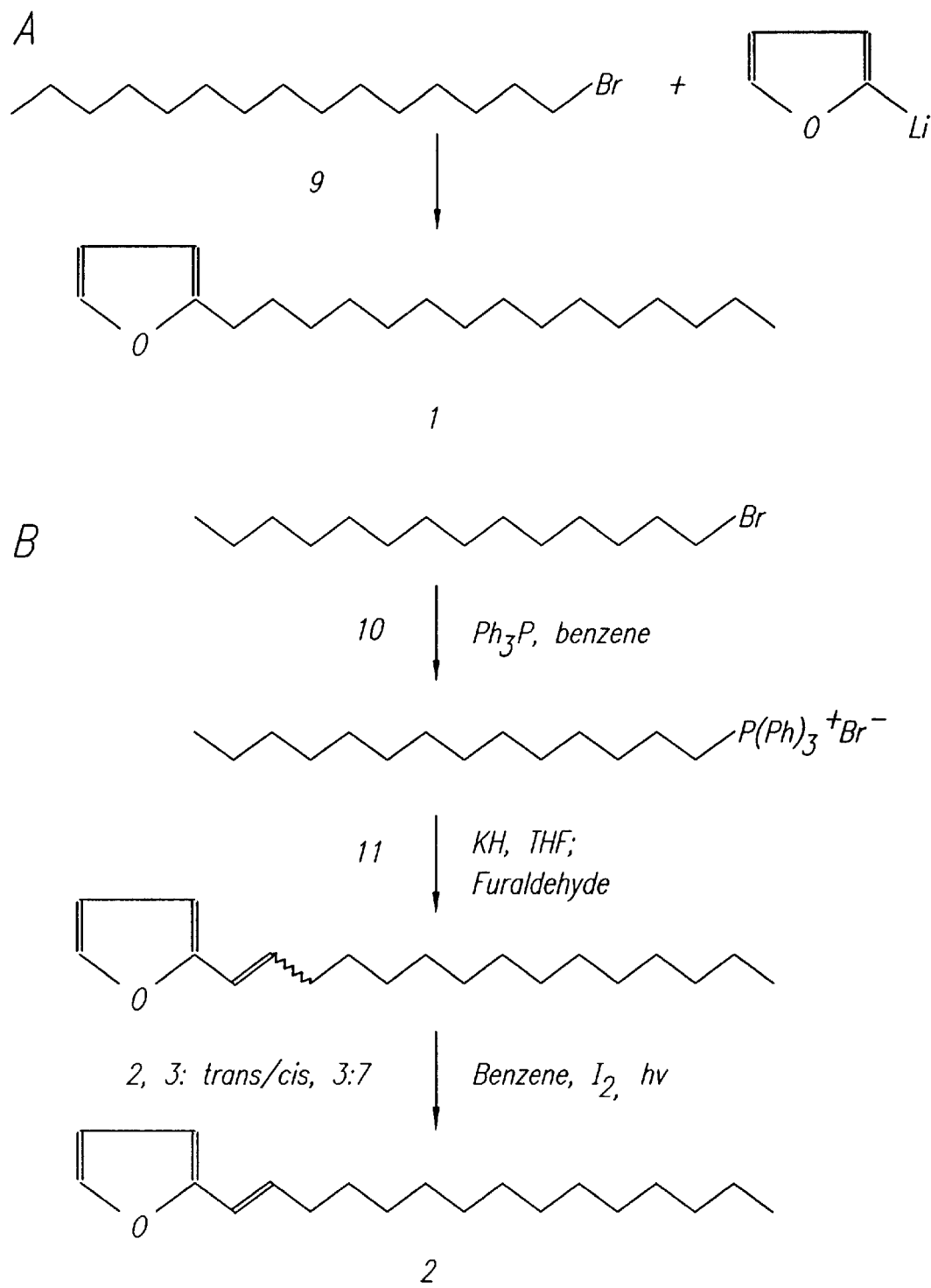

SCHEME 3
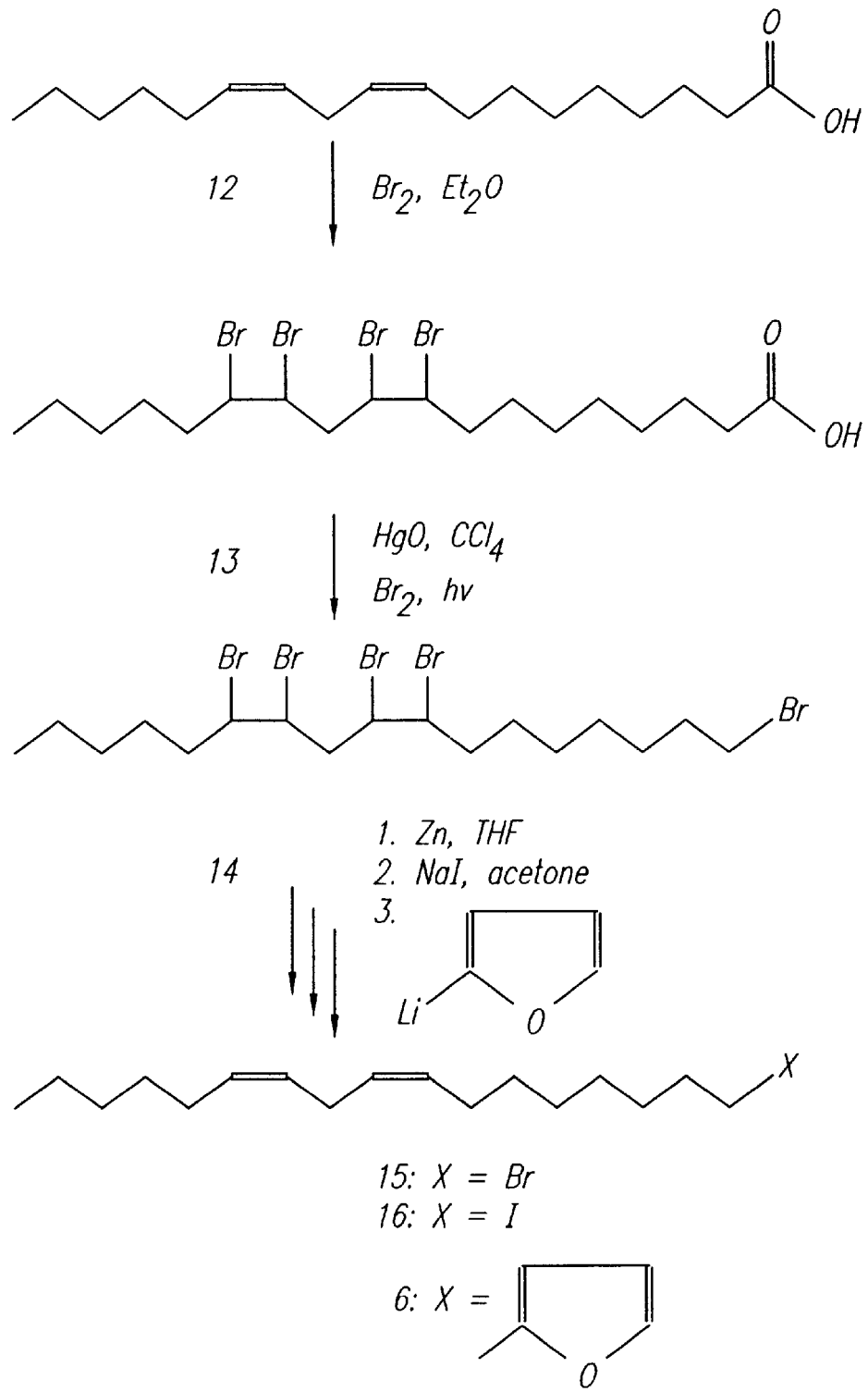

INSECTICIDAL AVOCADOFURANS AND TRIOLEIN

This application claims priority from Provisional Application No. 60/083,333 filed Apr. 27, 1998.

This invention was made with government support under National Science Foundation Grant No. DBC 8918964. The Government may have certain rights in this invention.

BACKGROUND OF THE INVENTION

1. Field of the Invention

This invention concerns novel insecticidal compounds isolated from specialized cells of the avocado. In particular, this invention concerns avocadofurans identified as 2-(tetradecyl)furan, 2-(pentadecyl)furan, 2-(hexadecyl)furan, 2-(heptadecyl)furan, 2-(octadecyl)furan, 2-(1EZ-pentadecenyl)furan, 2-(8Z,11Z-heptadecadienyl)furan, (8Z,11Z-heptadecadienyl)furan and the triglyceride triolein present in the avocado oil extracted from the avocado idioblast cells. These compounds inhibit larval growth and lengthen the larval development of insect pest and are highly synergistic, with a combination of any two compounds showing much greater toxicity than the same amount of any one alone.

2. Background Art and Related Disclosures

Agriculture of many states and countries is severely damaged by the crop pests. For example, in California, the beet armyworm, *Spodoptera exigua* is a key pest on lettuce and tomatoes. This pest is resistant to chlorinated hydrocarbons, cyclodienes, organophosphates and pyrethroids and has also demonstrated potential for resistance to the carbamate methomyl which is a predominant chemical used for its control. Moreover, even if effective, these chemicals are potentially hazardous to humans and animals and lately there has been pressure from public and from regulatory agencies to avoid using this kind of chemical insecticides.

Therefore, it would be advantageous to provide an efficient biocontrol of these type of pest using nontoxic insecticides.

Avocados, *Persea americana* Mill (Lauraceae), are oleaginous fruit in which oil levels in the mesocarp, or flesh, vary from 1–2% of fresh weight early in the season, to over 30% late in the season. The oils are valuable nutritionally as a source of energy, vitamins, and unsaturated lipids, with the edible portion of the fruit being rich in oleic, palmitic, linoleic, and palmitoleic acids as described in *The Biochemistry of Fruits and Their Products: The Avocado Pear*, Vol. 2: 1–63, A. C. Hulme (Ed.), Academic Press, London.

Several compounds isolated from avocado fruit have been reported to have various types of biological activity. For example, 1-acetoxy-2-hydroxy-4-oxo-heneicosa-(12Z,15Z)-diene (persin) extracted from the leaves of fresh avocado inhibited growth of 4th instar silkworm *Bombyx mori* L. larvae (*Agr. Biol. Chem.*, 39:1167 (1975), and *Jap. J. Appl. Entomol. Zool.*, 20:87 (1976)) at a concentration of 200 µg/g within 2 days. In 1982, persin was isolated from peels of unripe avocado fruit and found to possess an antifungal activity against *Colletotrichum gloeosporioides* Penz *Phytopat.*, 72:1578 (1982). Later on, a related compound, 1-acetoxy-2,4-dihydroxy-n-heptadec-16-ene, isolated from the peel and flesh of unripe avocado fruit, was also found to be active as a fungicide (*J. Phytopathol.*, 132:319 (1991)).

A further study identified a series of related compounds with antifungal activity, including 1,2,4-trihydroxyheptadec-16-yne, 1,2,4-trihydroxy-n-heptadec-16-ene, and 1-acetoxy-2,4-dihydroxyheptadec-16-yne, as described in *Phytochemistry*, 31:93 (1992).

Avocado leaves, seeds, roots and fruit were shown to contain specialized idioblast oil cells scattered throughout the avocado mesocarp, composing approximately 2% of the tissue volume. Moreover, these cells have been reported to contain an oil that differs from other lipids found in the fruit mesocarp.

Recent studies, described in *Physiol. Mol. Plant Pathol.*, 43:319 (1993) demonstrated the antifungal activity of two compounds present in these idioblast oil cells to the fungus, *C. gloeosporioides*.

Natural compounds containing furan rings are commonly found in many plant species. However, except for the specific phytochemicals such as furanocoumarins, few studies examined their biological role. A particular group of these furan derived plant compounds is present in avocados, *Persea americana* Mill (Kauraceae) and related plants. These compounds are commonly referred to as avocadofurans and were first isolated, identified and described in *Tetrahedron*, 25:4617 (1969). Two avocadofurans, namely 2-(trideca-12-ynyl)furan and 2-(trideca-12-enyl)furan, were isolated from avocado fruit and seeds. Later, other avocadofurans were isolated from seed extracts.

Although as compounds many avocadofurans were identified, their biological activity remained unexplored. The first report on some antibacterial activity appeared in 1970 when the growth inhibitory activity of 2-(trideca-12-enyl)furan against *Bacillus subtilis* and *Staphylococcus aureus* was reported.

Avocadofurans isolated from avocado leaves were also tested for their insecticidal activity against *Bombyx mori* L. However, their activity was very small, if any.

It has now been discovered that the fractions isolated from specific idioblast cells of avocado are potent nontoxic insecticides of insect pests.

It is, therefore, a primary subject of the invention to provide a new nontoxic insecticides which would be effective against common crop insect pest. The insecticides of the invention are avocadofurans having significant inhibitory bioactivity on the growth and development of the insect, particularly insect of generalists herbivore of *S. exigua* type.

All patents, patent applications and publications cited herein are hereby incorporated by reference.

SUMMARY OF THE INVENTION

One aspect of the current invention are novel avocadofurans and triolein insecticides.

Another aspect of the current invention are the insecticides identified, isolated and fractionated from the idioblast cell oil of avocado.

Still another aspect of the current invention are synthetically prepared insecticides previously isolated from the idioblast cell oil of avocado.

Still yet another aspect of the current invention are avocadofurans and triolein which have substantial toxicity for early instars of the generalists insect herbivore, *Spodoptera exigua* and other insect pests.

Still another aspect of the current invention are avocadofurans and triolein which have substantial toxicity for larvae and pupae of insect pests, identified as 2-(tetradecyl)furan, 2-(pentadecyl)furan, 2-(hexadecyl)furan, 2-(octadecyl)furan, 2-(heptadecyl)furan, 2-(1E-pentadecenyl)furan, 2-(8Z,11Z-heptadecadienyl)furan, and the triglyceride triolein.

Still yet another aspect of the current invention is an avocadofuran and triolein combination which shows synergistic insecticidal effect on S. exigua.

BRIEF DESCRIPTION OF FIGURES

FIG. 1 shows structures of compounds identified from avocado idioblast cell oil fractions.

FIG. 4 is a graph illustrating effects of synthetic avocadofurans or triolein on S. exigua larval development.

DEFINITIONS

Figure 2A:
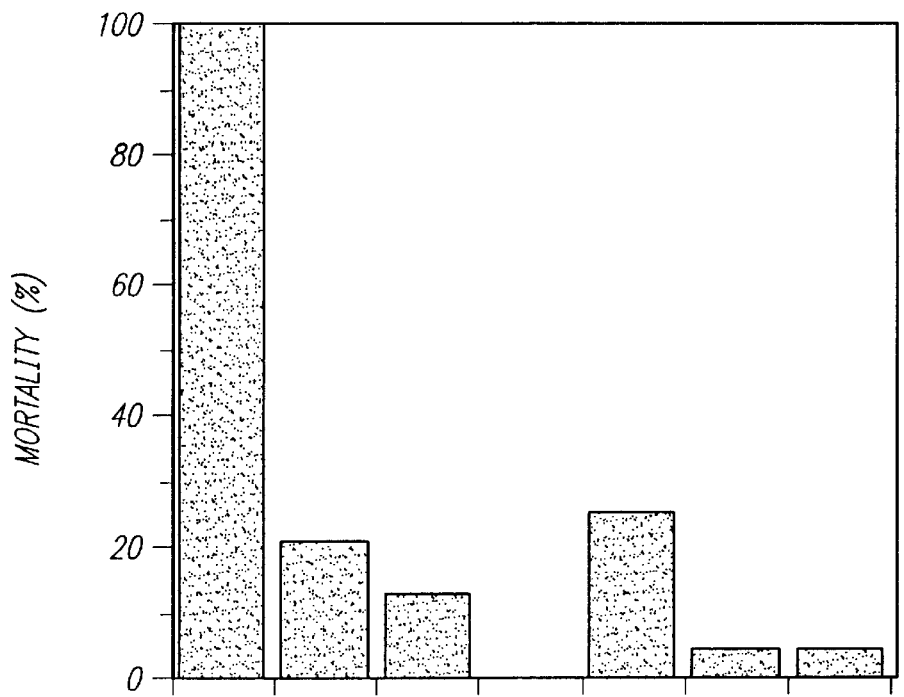
FIG. 2 are graphs illustrating percent of mortality (FIG. 2A) and weight (FIG. 2B) of S. exigua larvae fed control diet and diet containing flash chromatography fractions of avocado idioblast cell oil.

As used herein:

"Fraction 1-1, 1-2, etc," means the fraction isolated from the crude oil isolated from idioblast cells of avocado according to Scheme 1.

"Fraction" or "subfraction 1-1-1 through 1-1-12" means a fraction isolated from the fraction 1-1 according to Scheme 1.

"Compound" means a specific compound identified in the specification which may be a subfraction of compound 1-1, or a compound used in the synthesis of the avocadofurans. Thus compound (1) is, in fact, a subfraction 1-1-1, but compound (8) is a subfraction 1-1-12. Compound 13, for example is the tetrabromo acid used for preparation of compound (6). The fractions, subfractions and compounds should be identified and considered individually and separately.

DETAILED DESCRIPTION OF THE INVENTION

This invention concerns discovery of novel avocadofurans and triolein effective as potent nontoxic insecticides against insect pest larvae, particularly against larvae of Spodoptera exigua.

S. exigua was used as a model insect because it has such a broad host range. The material, however, has utility for other plant feeding insects with chewing mouthparts including many household pests which consume plant material, such as cockroaches, ants, etc.)and a bait formulation, in particular, would be effective also for these insects.

The avocadofurans compounds are isolated from specialized idioblast cells of avocado or synthetically prepared. Specifically, these compounds include 2-(tetradecyl)furan, 2-(pentadecyl)furan, 2-(hexadecyl)furan, 2-(heptadecyl) furan, 2-(octadecyl)furan, 2-(1E-pentadecenyl)furan, 2-(8Z, 11Z-heptadecadienyl)furan, and the triglyceride triolein, all isolated from the avocado idioblast cells. The avocadofurans and triolein significantly inhibit larval growth individually and show highly synergistic activity in combination of two or more, with a small amount of any two compounds showing much greater toxicity than a large amount of any one alone.

I. Avocado Oil and Fractions Isolated from Idioblast Cells

A. Avocado Oil Fractions and Subfractions

Avocado is oleaginous fruit containing specific cells or structures. The invention has focused on chemicals present in a specific cell type, namely in idioblast cells of avocado. Idioblast cells of avocado are thick-walled secretory structures that differentiate from the avocado parenchyma. Avocado leaves, seeds, roots and fruit contain specialized idioblast oil cells scattered throughout the avocado mesocarp. These cells contain an oil that differs from lipids present in cells of other avocado tissues. The oil of avocado idioblast cells was investigated and fractions having different insecticidal bioactivity were discovered.

Findings leading to the current invention indicated that the crude oil and two fractions extracted from idioblast cells were toxic to early ($LC_{50}$=1,600 $\mu$g/g) and late instars ($LC_{50}$=5,100 $\mu$g/g) of *Spodoptera exigua* and also deterred feeding.

The first fraction was identified as persin, 1-acetoxy-2-hydroxy-4-oxo-heneicosa-(12Z,15Z)-diene. The second fraction also showed inhibitory activity on the *S. exigua* larvae. This second fraction was then investigated in order to identify the biologically active subfractions of this second fraction, to test these subfractions for their biological activity, and to synthesize the active subfractions to provide bioactive inhibitors of larval growth of *S. exigua.*

B. Isolation and Identification of Active Compounds

Active avocadofurans were isolated from idioblast cells isolated from ripe avocados obtained from South Coast Research and Extension Center, University of California, Santa Ana, Calif.

Idioblast cells were separated from ripe fruit and the oil was extracted as described in Example 1, according to *J. Econ. Entomol.,* 89:15771 (1996).

Active avocadofurans of the invention were isolated and fractionated and identified as described in Example 2 and illustrated in Schemes 1–3, and then tested for their biological activity.

The crude idioblast cell oil was fractionated as shown in Scheme 1. Briefly, idioblast cells were extracted using a modification of the technique described by *Int. J. Plant. Sci.,* 153:301. The mesocarp from avocados was excised and placed in a blender with water. The tissue was homogenized until liquid. The blended mixture was then sieved through a 149-$\mu$ mesh screen followed by a 106-$\mu$ mesh screen. The substrate on the upper surface of the 106-$\mu$ mesh was washed with tap water until clean, and the filtrate was collected in large Erlenmeyer flasks. The filtrate, which was green because of the presence of large amounts of chlorophyll, was then poured through a 63-μ mesh screen. The idioblast cells remained on the upper surface of this screen. The cells were washed with tap water, until they were straw colored (pale brown), and then transferred to a flask.

To obtain the oil from the idioblast cells, a chloroform and methanol mixture was added to the flask containing the cells at a ratio of 1:2:1.8 (chloroform:methanol:cells). The mixture was stirred for 15–30 minutes before more chloroform was added to obtain a final ratio of 2:2:1.8. The mixture was stirred for at least 5 minutes more. The resulting material was poured into 30 ml centrifuge tubes and spun at 1.12–4.47 xg for 35 minutes. Centrifugation resulted in 3 solvent layers and the pellet. The more polar components that correspond to the 2 top layers were pipetted off. The bottom layer, containing the lipids dissolved in chloroform, was poured through filter paper No. 1 (Whatman, Maidstone, U.K.) to remove any pelleted material that might remain. The solvent was evaporated using a rotary evaporator. The extract was then submitted to flash chromatography as described in Example 3.

The initial steps of the fractionation have been previously described in $J.$ $Chem.$ $Ecol.,$ 23:1819 (1997). A portion of the crude oil (4.5 g) was fractionated by flash chromatography on silica gel (230–400 mesh; 5 cm I.D.×25 cm) (Aldrich Chemical, St. Louis, Mo.), eluting sequentially with 2-liter each of toluene; ethyl ether: acetic acid 70:30:1 (vol:vol:vol), 50:50:1, and 10:90:1. The material remaining on the column was then stripped off with ethanol (2-liter). Fractions were checked by think layer chromatography (TLC) on silica plates developed with toluene: ethyl ether: acetic acid (70:30:1 vol:vol:vol). Spots on developed plates were visualized using UV (254 nm) followed by spraying with $H_2SO_4$ and charring with a hot air blower. Subfractions were combined to yield 8 fractions which were concentrated under reduced pressure, followed by exposure to 0.5 mm Hg vacuum to remove traces of solvent. The concentrated fractions were weighed, then diluted with acetone to a final volume of 10 ml, and refrigerated at 4° C. until needed. Eight fractions were isolated from the crude oil extract as seen in Scheme 1. The lowest polarity fraction from the initial flash chromatographic separation, fraction 1, was present as 3.67 g of total weight. Fraction 3 was identified as persin.

The fraction 1 was further purified by flash chromatography column (5 cm I.D.×25 cm), eluted sequentially with 2 liters each of toluene: ethyl ether 95:5, and 90:10 (vol:vol). The remaining material on the column was stripped off with ethanol (2 liters). Fractions were checked by thin layer chromatography (TLC) on silica plates developed with toluene: ethyl ether (90:10 vol:vol). Spots on developed plates were visualized under UV light (254 nm), followed by spraying with $H_2SO_4$ and charring with a heat gun.

Fraction 1 was separated to yield 6 fractions 1-1 to 1-6, which were concentrated under reduced pressure, then pumped under vacuum (0.5 mm Hg) to remove traces of solvent. The concentrated fractions were weighed, then diluted with acetone to a final volume of 10 ml, and refrigerated at 4° C. until bioassayed.

From fractions 1-1 to 1-6, the fraction 1-1 was found to be present in largest amount of about 75%, present as 1.3 g total weight. This fraction (1-1) was further subfractionated by flash chromatography on column (5 cm I.D.×25 cm) eluted sequentially with 2 liters of hexane, 1 liter of hexane:ethyl ether 95:5 (vol:vol), 0.4 liter of hexane: ethyl ether 90:10, and 0.4 liter of ethyl ether. Fraction 1-1 yielded twelve subfractions 1-1-1 through 1-1-12. The twelve fractions were collected, concentrated, and tested for biological activity.

As shown in Scheme 1, subfractions 1-1-4 (0.08 g), 1-1-8 (0.09 g), and 1-1-12 (0.89 g) contained most of the mass of material (6%, 7% and 68%, respectively), and were also found to be most active in bioassays. From these three subfractions, eight compounds were isolated and identified.

Structures of the eight identified compounds isolated from avocado idioblast cells are shown in FIG. 1. Physical data for these fractions are given in Example 5–14.

Fraction 1-1-4 yielded 39.2% of compound (1), namely 2-(pentadecyl)furan, 49.4% of compound (2), namely 2-(1E-pentadecenyl)furan, 2.8% of compound (3), namely 2-(1Z-pentadecenyl)furan, 2.6% of compound (4), namely 2-(heptadecyl)furan, and 6% of compound (5), namely 2-(1E-heptadecenyl)furan. The identification of these compounds was confirmed by synthesis.

Fraction 1-1-8 yielded 83% of compound (6), namely 2-(8Z,11Z-heptadecadienyl)furan and 17% of compound (7), namely 2-(1E, 8Z,11Z-heptadecatrienyl)furan.

Fraction 1-1-12 was identified as triolein, compound (8).

D. Synthesis of Furan Compounds

Syntheses of the above identified avocadofurans is described in detail in Examples 5–14.

The 2-(alkyl and alkenyl)furans of this invention can be prepared by selecting the proper branched or linear C10 to C20 saturated or unsaturated alkyl or alkenyl compound and reacting it with a furan, such as a 2-lithiofuran in a polar solvent, such as tetrahydrofuran (THF).

Briefly, for example, synthesis of saturated C15 and C17 2-(alkyl)furans, such as compounds (1) and (4) were achieved by the coupling of the appropriate bromoalkanes with 2-lithiofuran in THF. Both of the low-melting saturated alkylfurans were recrystallized in methanol, allowing easy purification on multigram scale.

2-(1E-pentadecenyl)furan, compound (2) and its Z isomer compound (3) were prepared by Wittig reaction of the ylide prepared from tetradecyl triphenylphosphonium bromide with furfural, according to Scheme 2B, to afford a 7:3 mixture of Z and Z isomers. Photochemical isomerization of the mixed isomers in benzene with iodine catalysis, followed by recrystallisation from methanol, gave the E-isomer compound (2) in greater than 97% purity.

In the first step of the synthesis of doubly unsaturated furan, such as compound (6), seen in Scheme 3, linoleic acid (12) was treated with bromine to afford the tetrabromo acid (13). Using a modification of the Hunsdiecker reaction, compound (13) was decarboxylated to give pentabromide (14). Regeneration of the diene moiety with zinc powder in THF yielded bromo diene (15), which was converted to the compound (16), and then coupled with 2-lithiofuran to afford the doubly unsaturated avocadofuran (6).

C. Biological Activity and Toxicity Studies

Avocadofurans of the invention identified above were tested for their insect growth inhibitory activity and their toxicity to insect was also studied.

Results of these studies are seen in FIGS. 2–4.

Figure 2B:
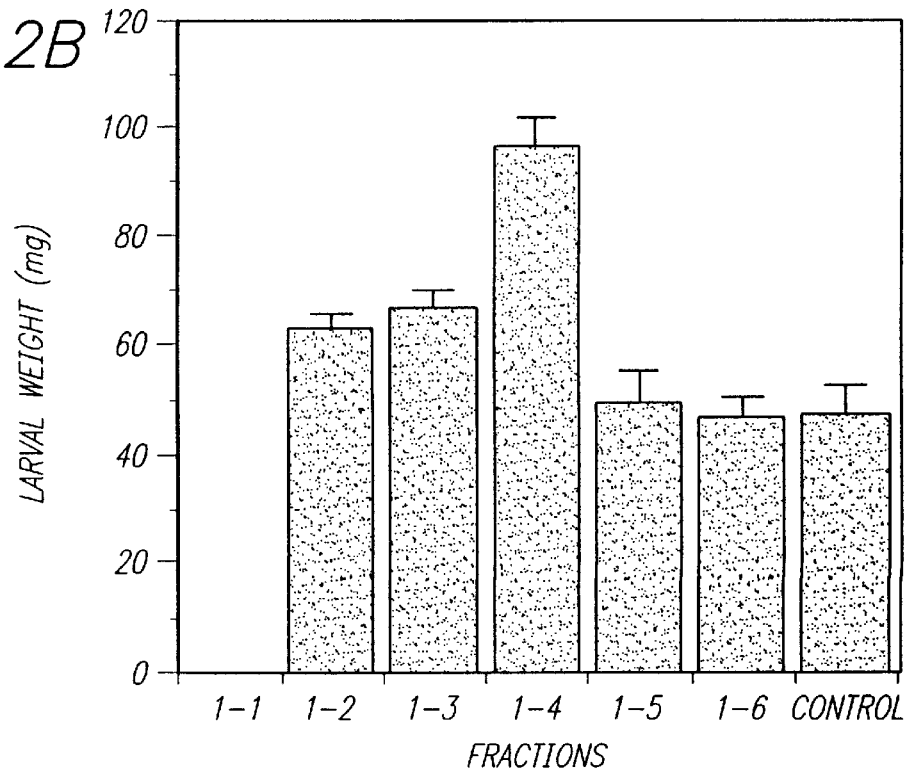

FIG. 2 are graphs illustrating percent of mortality (FIG. 2A) and weight (FIG. 2B) of $S.$ $exigua$ larvae fed control diet and diet containing flash chromatography fractions 1-1 to 1-6 (Scheme 1) of avocado idioblast cell oil. Different letters indicate statistical differences between treatments using Tukey's Pairwise Comparison Test, (P<0.05). Fractions were bioassayed at concentrations equivalent to 20 mg crude oil per ml of artificial diet.

On biological testing, the least polar fraction from the first two flash chromatographic steps, fraction 1-1 (FIG. 2AI), seen also in Scheme 1, produced 100% larval mortality as illustrated in FIG. 2A. Other fractions 1-2 through 1-6 (II–VI) produced only slight increase in mortality. The second best compounds was compound 1-5 (V), which had about 25% mortality followed by compound 1-2, which had about 20% mortality.

Since the fraction 1-1 had 100% mortality and did not increase the weight of the larvae, further fractionation of fraction 1-1, as observed in Scheme 1, was undertaken. Such fractionation yielded twelve subfraction of which three active subfractions (1-1-4, 1-1-8 and 1-1-12) have good mortality activity. Results are seen in FIG. 3.

Figure 3A:
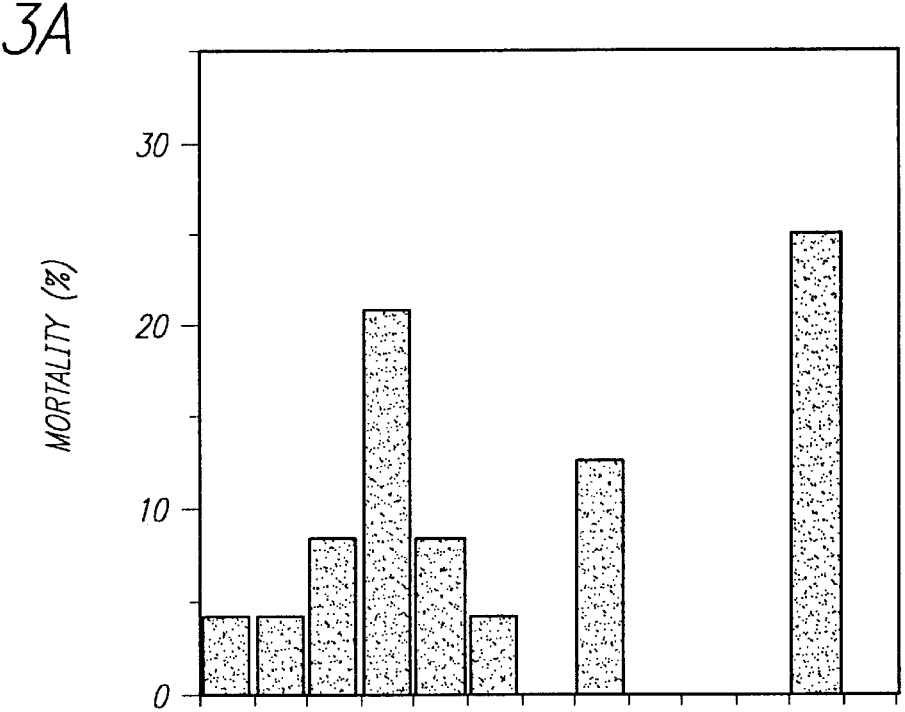
FIG. 3 are graphs illustrating percent of mortality (FIG. 3A) and weight (FIG. 3B) of S. exigua larvae fed control diet and diet containing subfractions of fractions 1-1.
Figure 3B:
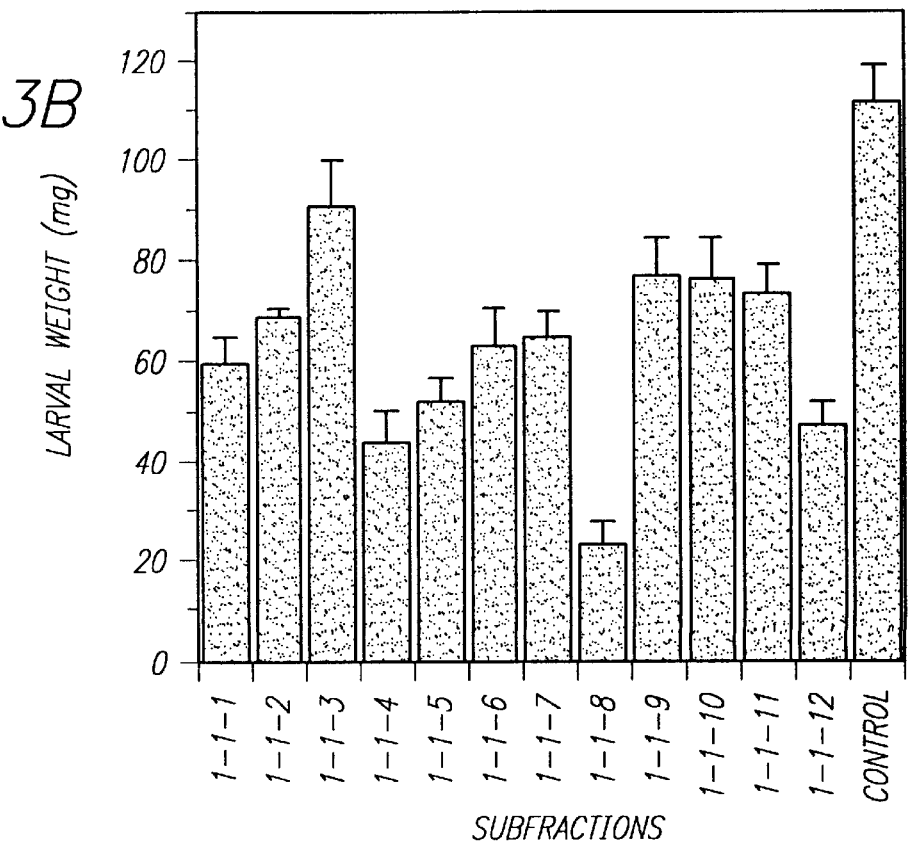

FIG. 3 are graphs illustrating percent of mortality (FIG. 3A) and weight (FIG. 3B) of *S. exigua* larvae fed control diet and diet containing one of twelve subfractions of the fraction 1-1. Different letters indicate statistical differences between treatments (Tukey's Pairwise Comparison, P<0.05). Fractions were bioassayed at concentrations equivalent to 20 mg crude oil per ml of artificial diet.

As seen in FIG. 3B, each of the three subfractions, namely 1-1-4, which includes compounds (1), (2), (3), (4) and (5), 1-1-8 which includes compounds (6) and (7) and 1-1-12, which is compound (8), significantly (P<0.05) reduced larval weight compared to control larvae in feeding bioassays, although, as seen in FIG. 3A, their larval mortality was lower than 30%. Subfractions 1-1-7, 1-1-9, 1-1-10 and 1-1-11 did not show any effect on the larval mortality and had small decreasing effect on the larval weight.

Table 1 and FIG. 4 show the growth inhibitory activity and mortality effects of the insecticidal compounds of the invention found in each of the three active subfractions 1-1-4, 1-1-8, and 1-1-12.

The growth inhibitory activity and mortality effects of the insecticidal compounds of the invention found in each of the three active subfractions 1-1-4, 1-1-8, and 1-1-12 is seen in FIG. 3. Of these subfractions, compound (1), 2-(pentadecyl)furan, present in subfraction 1-1-4, was the most active of the two major compounds from that subfraction. Furan (1) significantly inhibited larval growth as shown in Table 1, and at concentrations above 600 $\mu$g/g, reduced larval development by >70%. Relative Growth Index (RGI), expressed as log ($\mu$g/g) is seen in FIG. 4.

FIG. 4 is a graph illustrating effects of synthetic avocadofurans or triolein on *S. exigua* larval development. In FIG. 4, filled circles show response to 2-(pentadecyl)furan (y=5.66–1.79*log(x), $r^2$=0.94); filled squares show response to 2-(heptadecyl)furan (y=4.82–1.47*log(x), $r^2$=0.89); and open squares show response to triolein (y=7.68–1.83*log(x), $r^2$=0.86). The $LC_{50}$ (95% FL) (fiducial limits) was 1031 $\mu$g/g (988–1084 $\mu$g/g) of furan (1) in diet, with a log dose-probit regression line slope of 7.44 t 0.84.

The other major component present in subfraction 1-1-4, 2-(1E-pentadecyl)furan compound (2), showed biological activity only at concentrations approximately 3 times higher than furan (1), inhibiting *S. exigua* growth at concentrations of 3,500 $\mu$g/g or higher. At 3,500 $\mu$g/g, larval growth was reduced by 57.3% compared to the controls, but mortality was only 12.5%.

2-(heptadecyl)furan compound (4) was present as a minor component of subfraction 1-1-4, and it significantly inhibited larval growth as seen in Table 1. Although mortality was lower the 15% at concentrations between 600 and 900 $\mu$g/g, larval development and growth were significantly reduced (>75%) at these concentrations (Table 1). The $LC_{50}$ (95% FL) of 2-(heptadecyl)furan in diet was 1206 $\mu$g/g (1165–1273 $\mu$g/g), with a log dose-probit regression line slope of 14.03 t 2.29, seen in FIG. 4.

TABLE 1

Growth inhibitory and mortality effects of synthetic compounds from avocado idioblast oil cells to *S. exigua* larvae

| Concentration ($\mu$g/g) | 7-dLarval Weight[1] (Mean {mg] + SE) | 7-d Instar[1] (Mean + SE) | $GI^2$ | EC2 (%) | Mortality (%) |
|---|---|---|---|---|---|
| 2-(pentadecyl)furan (1) | | | | | |
| 600 | 8.50 ± 0.95 b | 2.29 ± 0.07 c | 0.69 | 72.89 | 9.37 |
| 750 | 4.44 ± 0.45 ab | 2.04 ± 0.07 bc | 0.55 | 85.83 | 18.75 |
| 900 | 3.03 ± 0.35 ab | 1.74 ± 0.07 ab | 0.26 | 90.35 | 32.29 |
| 1050 | 1.41 ± 0.15 a | 1.61 ± 0.07 a | 0.25 | 95.50 | 54.17 |
| 1200 | 1.32 ± 0.19 a | 1.56 ± 0.09 a | 0.15 | 95.78 | 71.87 |
| 2-(heptadecyl)furan (4) | | | | | |
| 600 | 6.44 ± 0.44 b | 2.25 ± 0.06 c | 0.73 | 79.46 | 2.08 |
| 750 | 4.03 ± 0.44 ab | 1.95 ± 0.06 b | 0.62 | 87.14 | 4.20 |
| 900 | 3.19 ± 0.30 ab | 1.87 ± 0.06 b | 0.56 | 89.84 | 10.42 |
| 1050 | 2.02 ± 0.16 a | 1.65 ± 0.07 ab | 0.46 | 93.55 | 16.67 |
| 1200 | 1.28 ± 0.16 a | 1.43 ± 0.08 a | 0.23 | 95.93 | 54.17 |
| Triolein (8) | | | | | |
| 7000 | 10.84 ± 1.42 ab | 2.35 ± 0.08 c | 0.64 | 65.43 | 18.75 |
| 8000 | 17.67 ± 2.05 b | 2.70 ± 0.10 bc | 0.67 | 43.64 | 26.04 |
| 9000 | 4.88 ± 0.65 a | 1.91 ± 0.08 ab | 0.39 | 84.44 | 40.63 |
| 10000 | 5.79 ± 0.96 a | 1.87 ± 0.10 a | 0.37 | 81.52 | 42.71 |
| 11000 | 8.82 ± 2.22 ab | 1.95 ± 0.13 a | 0.28 | 71.85 | 59.37 |
| Control | 31.35 ± 2.13 c | 3.19 ± 0.07 d | 1.03 | | 3.57 |

[1]Treatments with the same letter within each compound are not significantly different from each other (Tukey's Pairwise Comparisons, P < 0.05).
[2]GI = growth index,
EC = effective concentration; see text for calculations.

The major component in subfraction 1-1-8, 2-(8Z,11Z-heptadecadienyl)furan compound (6), was active only at concentrations of 1600 µg/g or higher, which was twice as high as the saturated compound (4). At 1600 µg/g, S. exigua growth was inhibited by 54.51% compared to control larvae, but mortality was small at lower than 5%.

Triolein, the major component in subfraction 1-1-12, significantly inhibited larval growth at relatively high concentrations as seen in Table 1, but larval weight was not linearly correlated with concentration. Concentrations of 7000 µg/g or higher significantly reduced larval weight and development. The $LC_{50}$ (95% FL) of triolein in diet was 10364 µg/g (9813-11277 µg/g), with a log dose-probit regression line slope of 5.75 f 0.94.

The results obtained with known or novel avocadofurans isolated from avocado idioblast cells show that these compounds are potent insecticidal agents causing a significant mortality rate in larvae on S. exigua and decrease of the larval weight.

As described above, bioassay-driven fractionation of crude avocado idioblast oil resulted in the identification of five compounds which were toxic to larvae of S. exigua. Four of these belonged to the previously known avocadofurans. The fifth compound, the common triglyceride triolein, is a general constituent of the avocado mesocarp and composes 15.8% of the total triglyceride composition of avocado mesocarp. Three other previously unknown avocadofurans, namely compounds (3), (5) and (7) were identified as minor components of fractions 1-1-4 and 1-1-8.

Although the isolated, identified and tested avocadofurans of the invention are structurally similar, they showed differences in their toxicity and growth inhibition effects. The two saturated avocadofurans compounds (1) and (4) were more toxic and growth inhibitory to S. exigua than either of the unsaturated compounds (2) and (6). Of these, compound (1) was the most toxic, as seen in FIG. 4.

Furthermore, these avocadofurans appear to be active as antifeedants at substantially lower (sublethal) concentrations, as demonstrated by the growth inhibition effects seen in FIG. 3B. Both the mortality and antifeedant effect of these avocadofurans is novel and unexpected.

Similarly, triolein or other triglycerides have never been reported to have deleterious effects on insects, and the toxicity exhibited by triolein at levels of about 1% in artificial diet was also unexpected. Furthermore, studies described below also indicated strong synergism between triolein and the avocadofurans.

II. Toxicity and Synergistic Interactions

As described above, avocadofurans showed high mortality rates and antifeedant effect on S. exigua. Further, in extended studies, their and their analogs toxicity as well as their synergism was investigated.

A. Toxicity of Avocadofurans and Furan Analogs

To determine the toxicity of avocadofurans and their furan analogs, five saturated furans of variable side chain lengths, namely 2-(tetradecyl)furan compound (20), 2-(pentadecyl) furan (1), 2-(hexadecyl)furan compound (21), 2-(heptadecyl)furan (4), and 2-(octadecyl)furan compound (22) were tested for their activity against S. exigua in diet assay. Diets for treatments were prepared at a concentration known to be insecticidal against S. exigua early instar of 5 µmoles $g^{-1}$ diet. To compare toxicity among furans, concentration in µmoles $g^{-1}$ diet were adjusted according to the molecular weights of individual furans. Bioassays were as described in Examples.

Of the five compounds investigated, 2-(tetradecyl)furan, 2-(hexadecyl)furan and 2-(octadecyl)furan have never before been reported to occur in either the avocado fruit or in related plants and their use as the insecticide is therefore novel and unexpected. Results of these studies, described in detail in Example 20, are illustrated in FIG. 5.

Figure 5A:
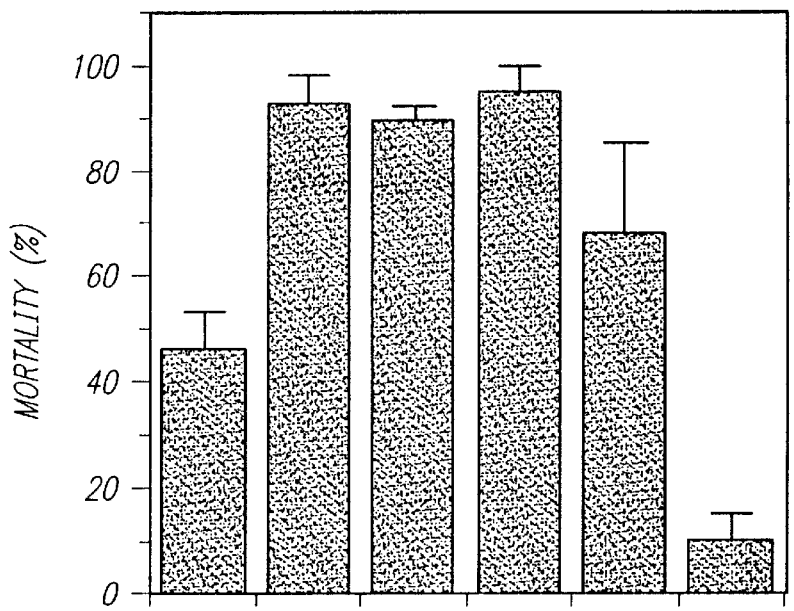
FIG. 5 are graphs illustrating percent of mortality (FIG. 5A) and weight (FIG. 5B) of S. exigua larvae fed with different furans incorporated in diet at 5 $\mu$moles g$^{-1}$.
Figure 5B:
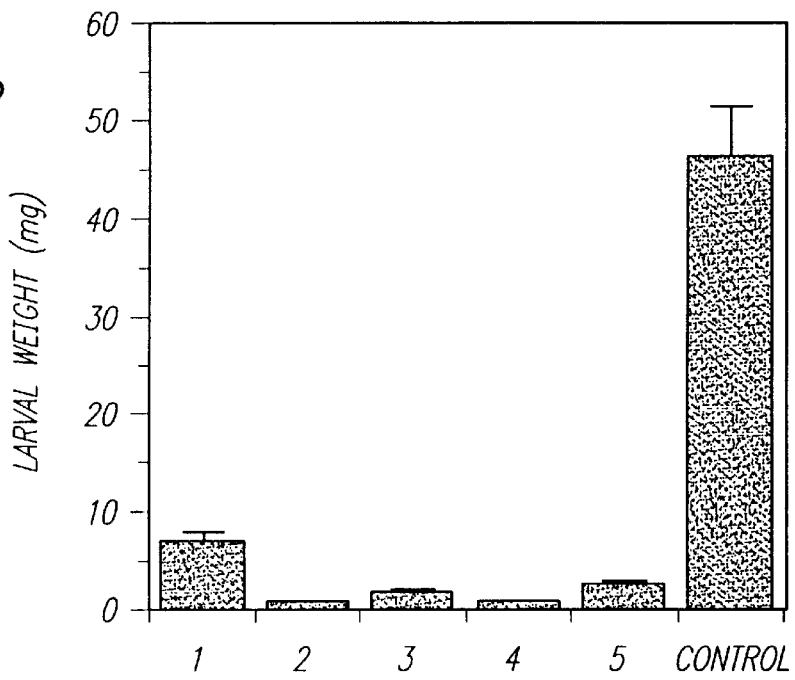

FIG. 5 are graphs illustrating percent of mortality (FIG. 5A) and weight (FIG. 5B) of S. exigua larvae fed with different furans incorporated in diet at 5 µmoles $g^{-1}$. Bars represent standard errors. Treatments means with same letters are not significantly different at 5% level (Tukey Compromise Test).

Results presented in FIG. 5 show that all assayed furans significantly reduced 9-day larval weight (P<0.001, F=16.15, df=5,184) and increase mortality (P<0.001, F=14.39, df=5,18) compared to controls at a concentration of 5 µmoles $g^{-1}$ of diet. Of the furan tested, 2-(tetradecyl) furan compound (20) had the lowest activity, killing less than 50% of S. exigua larvae, but significantly reducing larval weight compared to the control. All other four tested furans have a very high mortality and therefore toxicity against S. exigua larvae. The larval weight reduction of two new analogs, namely 2-(hexadecyl)furan compound (21) and 2-(octadecyl)furan compound (22) was comparable to the best compound described above, namely compound (1).

B. Toxicity of Individual Avocadofurans and Triolein

In this study, individual activity of avocadofurans was investigated quantitatively. For this purpose, eight concentrations of the avocadofurans (1) and (4) and triolein (8) were tested. Results are seen in FIG. 6.

Figure 6A:
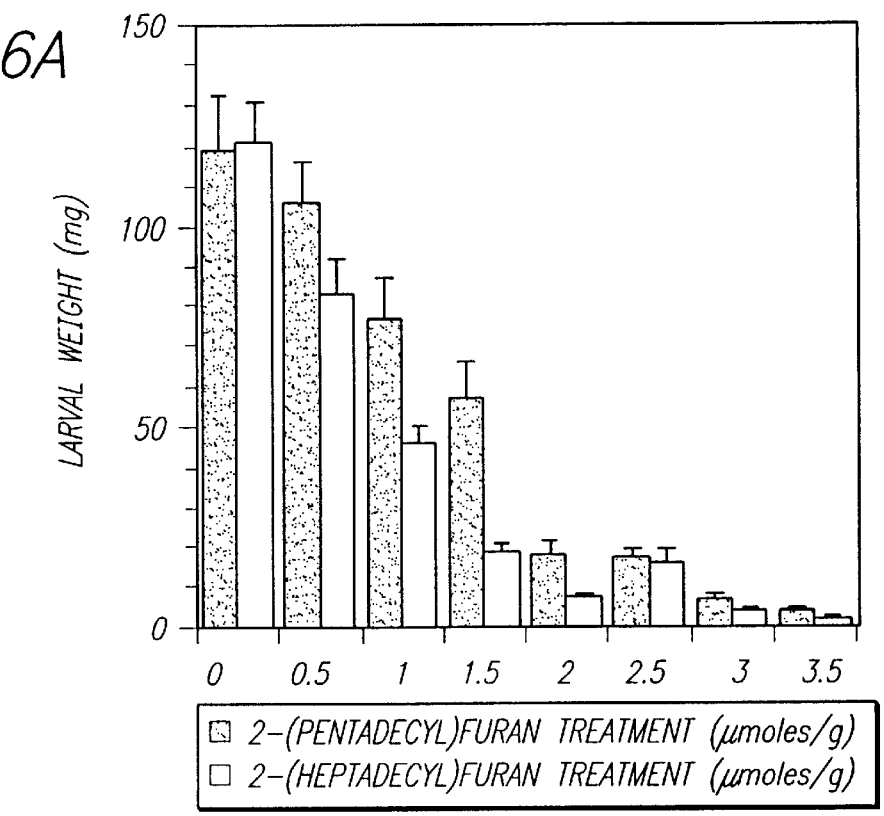
FIG. 6 are graphs showing effect of increasing concentrations of 2-(pentadecyl)furan and 2-(heptadecyl)furan (FIG. 6A) and triolein (FIG. 6B) on S. exigua larval weight.
Figure 6B:
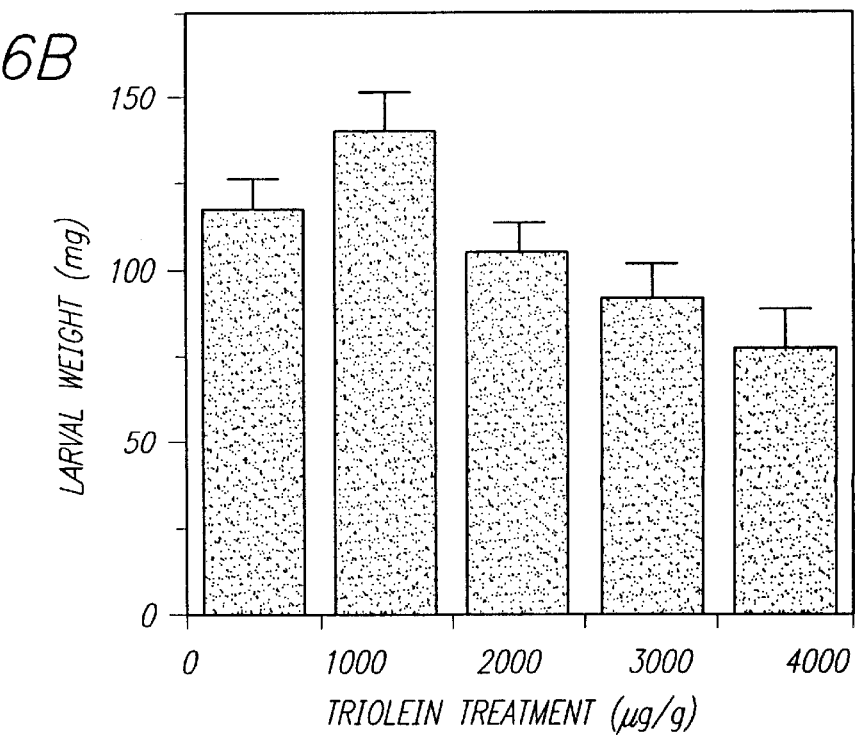

FIG. 6 are graphs showing effect of increasing concentrations 0, 0.5, 1, 1.5, 2, 2.5, 3, and 3.5 µmoles $g^{-1}$ of diet of 2-(pentadecyl)furan (1) and 2-(heptadecyl)furan (4), seen in FIG. 6A and 0, 1,000, 2,000, 3,000 and 4,000 µg $g^{-1}$ of diet of triolein (8), seen in FIG. 6B, on S. exigua larval weight.

In general, the two saturated avocadofurans significantly decreased S. exigua larval weight as compared to controls at high concentrations. Compound (1) significantly reduced 9-day larval weights at concentrations of 1.5 µmoles $g^{-1}$ or higher compared to controls (P<0.001, F=17.46, df=7,333). At these concentrations growth was inhibited by more than 50%, as seen in FIG. 6A.

Triolein, seen in FIG. 6B, was inhibitory at concentrations much higher than either of the avocadofurans tested in this assay. Compared to controls, 9-d S. exigua weight was significantly reduced by more than 35% at low concentrations of 2,000 µg $g^{-1}$ or higher (P<0.001, F=5.12, df=4,236.

In similar experimental set, the weight of pupae, and times of pupation were also followed. Effect of increasing concentration of avocadofurans on pupal weights is seen in FIG. 7.

Figure 7A:
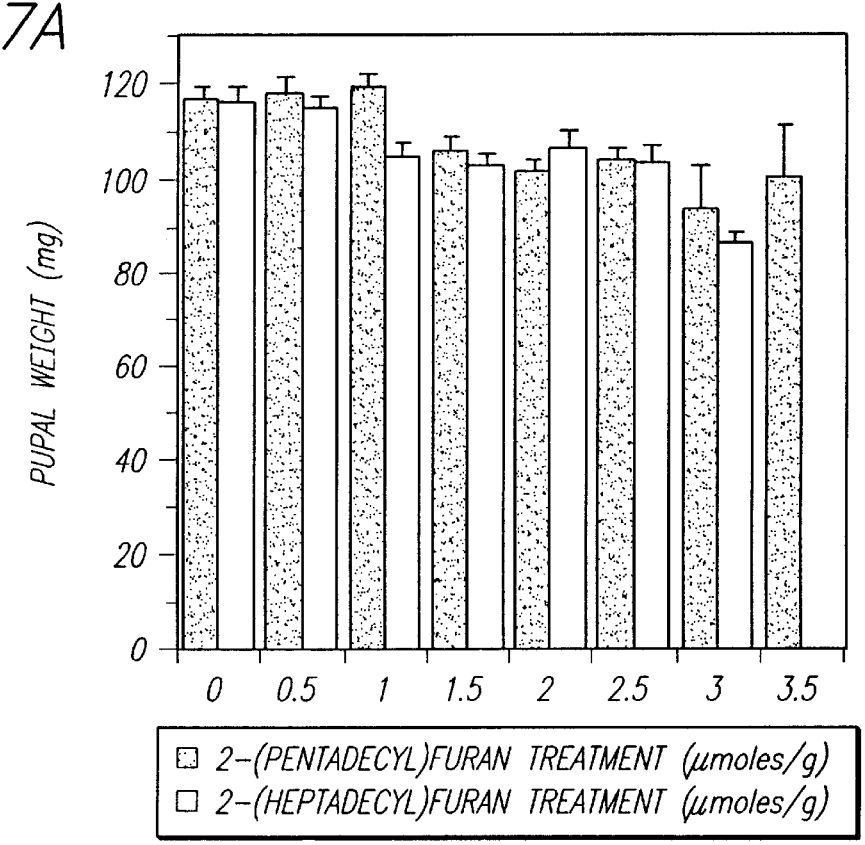
FIG. 7 are graphs showing effect of increasing concentrations of 2-(pentadecyl)furan and 2-(heptadecyl)furan (FIG. 7A) and triolein (FIG. 7B) on S. exigua pupal weight.

FIG. 7A is a graph showing effect of increasing concentrations of 2-(pentadecyl)furan (1) and 2-(heptadecyl)furan (4) on S. exigua pupal weight. Bars represent standard errors.

As seen in FIG. 7A, pupal weights were also significantly reduced as 2-(pentadecyl)furan (1) and 2-(heptadecyl)furan (4) concentrations increased in the diet. Compared to control larvae, both compounds (1) and (4) significantly reduced pupal weight at concentrations of 3 $\mu$moles $g^{-1}$ or higher in diet.

Figure 7B:
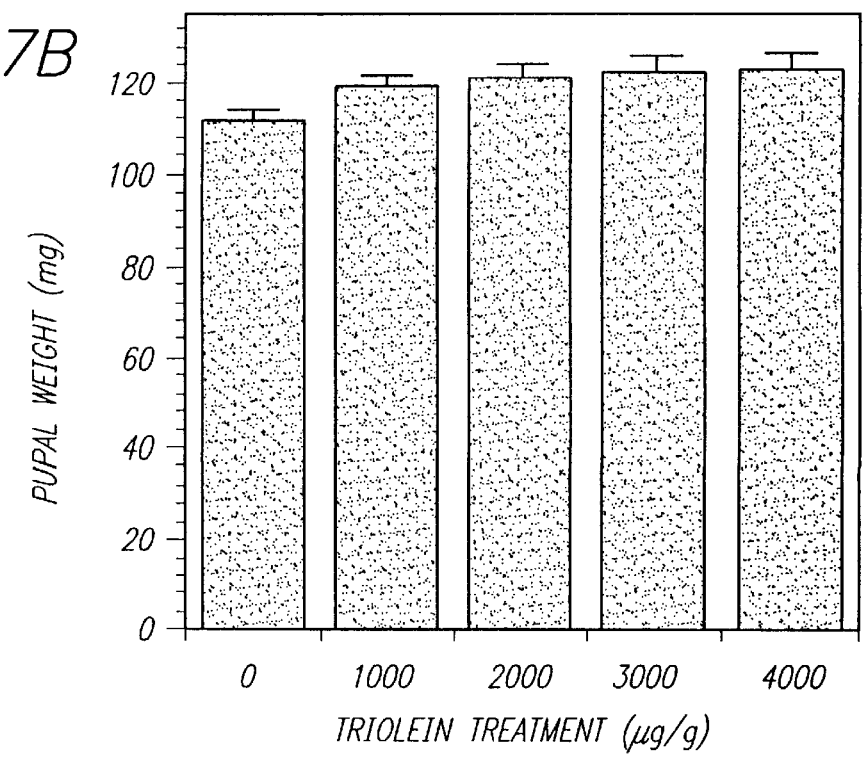

FIG. 7B is a graph showing effect of increasing concentrations of triolein on S. exigua pupal weight. Bars represent standard errors. As seen in FIG. 7B, increasing concentrations of triolein up to 4,000 $\mu g$ $g^{-1}$ in diet had no effect on pupal weight (P=0.714, F=2.19, df=4,196).

Larval developmental time from neonate to pupa was also measured and results are seen in FIG. 8.

Figure 8A:
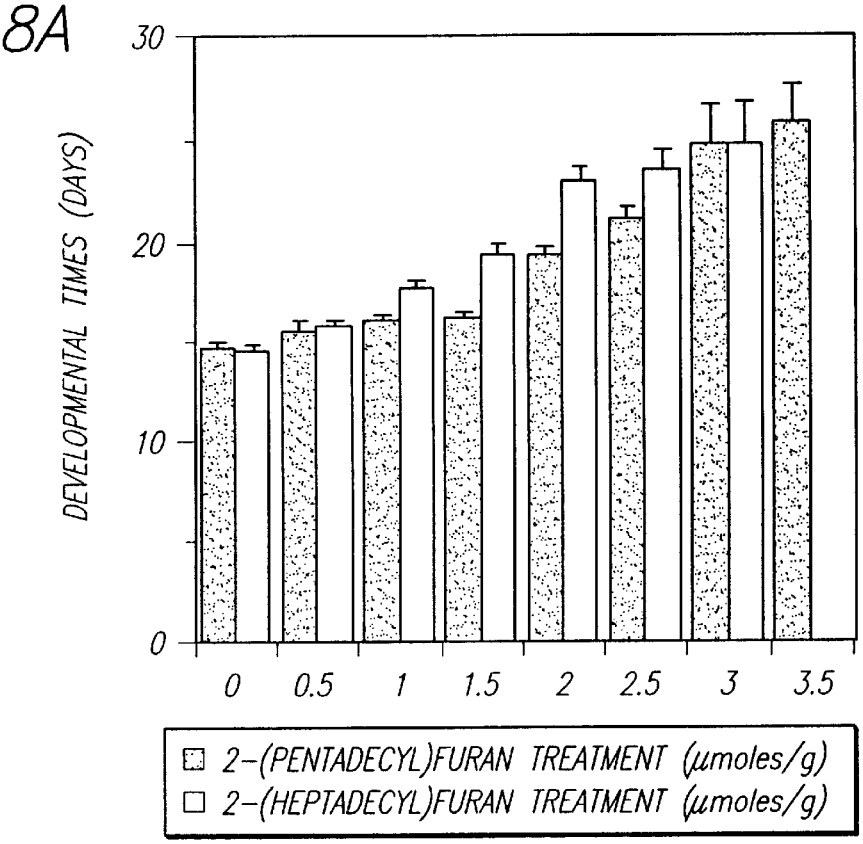
FIG. 8 are graphs showing effect of increasing concentrations of 2-(pentadecyl)furan and 2-(heptadecyl)furan (FIG. 8A) and triolein (FIG. 5B) on S. exigua development times from neonate to pupa.
Figure 8B:
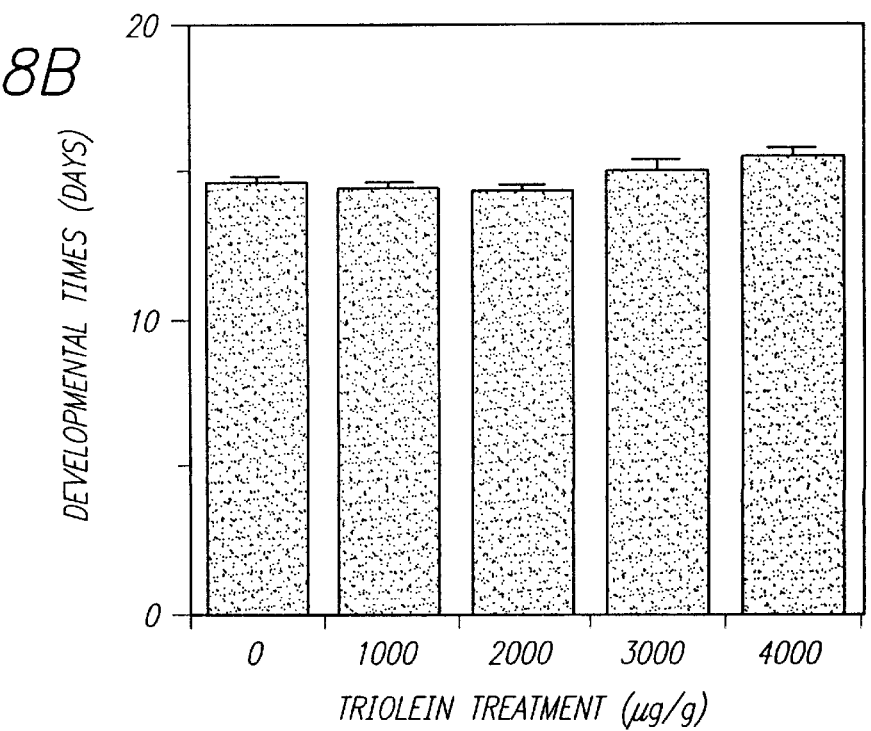

FIG. 8 are graphs showing effect of increasing concentrations of 2-(pentadecyl)furan and 2-(heptadecyl)furan (FIG. 8A) and triolein (FIG. 8B) on S. exigua development times from neonate to pupa.

As seen in FIG. 8A, larval developmental time from neonate to pupa was significantly prolonged as dietary concentrations of 2-(pentadecyl)furan, compound (1), (P<0.001, F=29.54, df=7,273) and 2-(heptadecyl)furan (4) (P<0.001, F=40.57, df=6,299) increased.

As seen in FIG. 8B, however, larval developmental time from neonate to pupa was not significantly prolonged as dietary concentrations of triolein (P 1.01, F=1.96, df=4,196) increased.

Increased rates of avocadofurans in diet increased larval mortality, similarly to studies described above in Section I. Results of these studies are seen in FIG. 9.

Figure 9A:
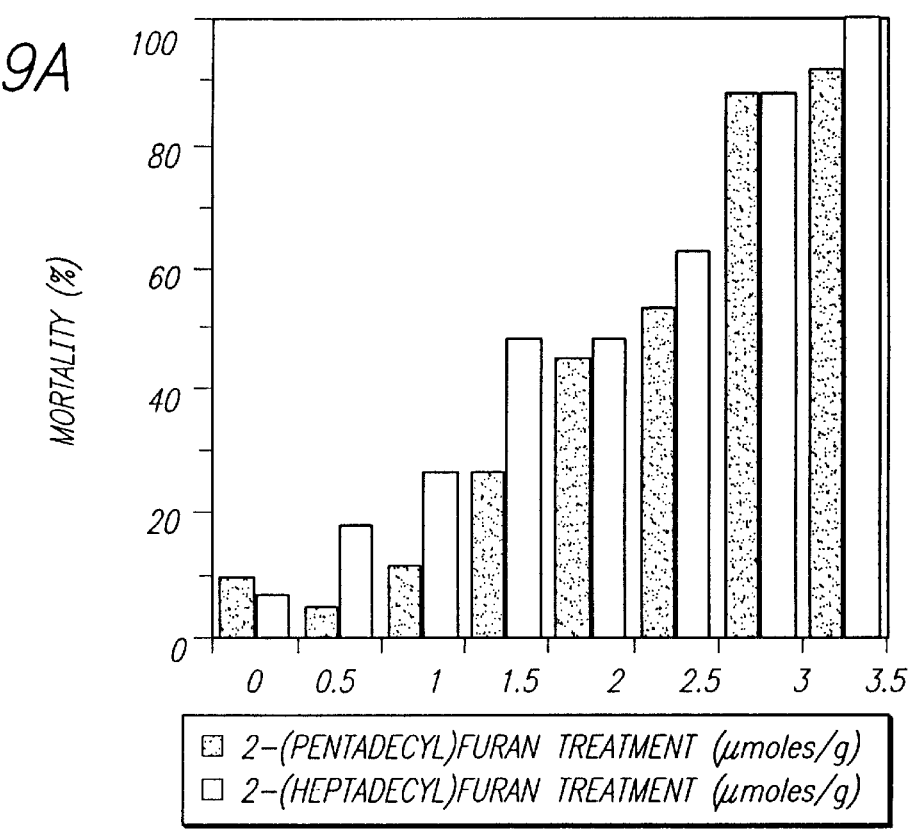
FIG. 9 are graphs showing effect of increasing concentrations of 2-(pentadecyl)furan and 2-(heptadecyl)furan (FIG. 9A) and triolein (FIG. 9B) on S. exigua mortality during the larval stage.
Figure 9B:
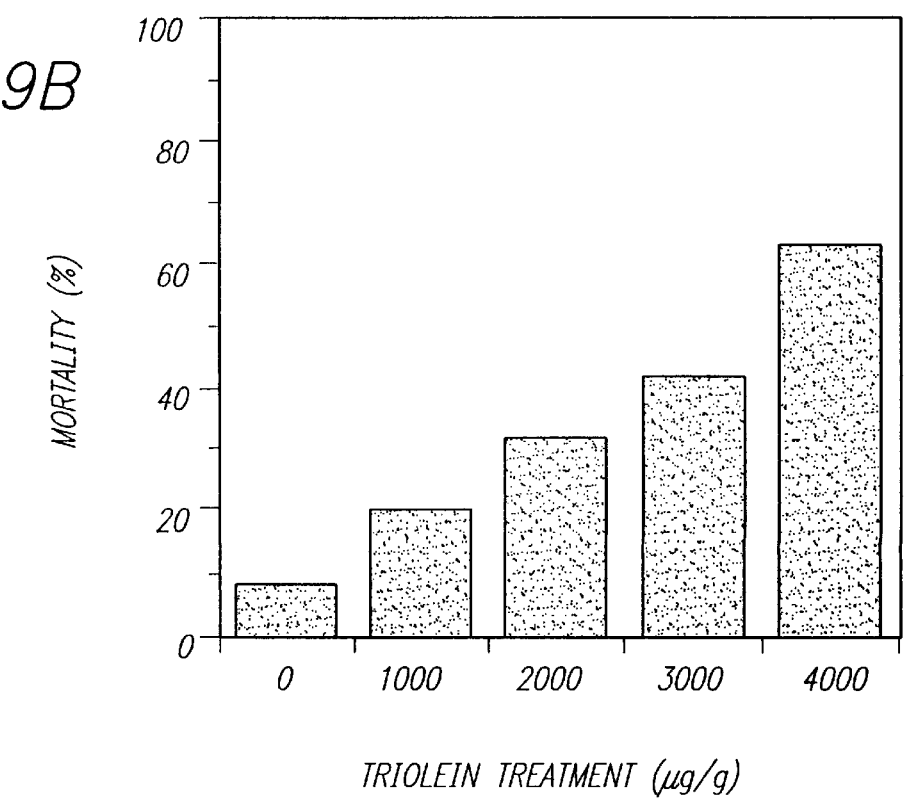

FIG. 9 are graphs showing effect of increasing concentrations of 2-(pentadecyl)furan (1) and 2-(heptadecyl)furan (4), seen in FIG. 9A and triolein (8) seen in FIG. 9B on S. exigua mortality during the larval stage from egg hatch to pupation.

As seen in FIG. 9A, the $LC_{50}$ for 2-(pentadecyl)furan (1) and 2-(heptadecyl)furan (4) were 2.2 and 2.1 moles $g^{-1}$ diet for the larval stage. These results are also seen in Table 2.

Although triolein had no effect on larval developmental time and pupal weight, increasing concentrations of triolein increases larval mortality. The $LC_{50}$ for triolein was 3,631 $\mu g$ $g^{-1}$ in diet for the larval stage. Results are also seen in Table 2.

The Relative Growth Index (RGI) values for both 2-(pentadecyl)furan (1) and 2-(heptadecyl)furan (4) and triolein (8) decreased with increasing concentrations of avocadofurans and triolein as seen in FIG. 10.

Figure 10A:
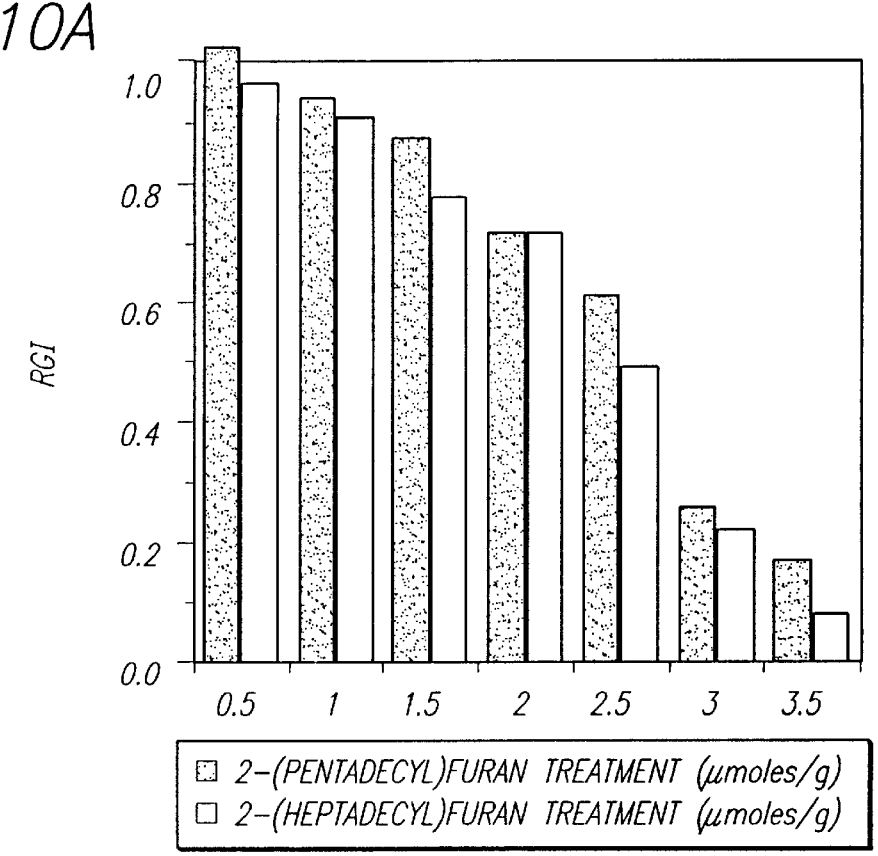
FIG. 10 are graphs showing effect of increasing concentrations of 2-(pentadecyl)furan and 2-(heptadecyl)furan (FIG. 10A) and triolein (FIG. 10B) on the Relative Growth Index (RGI) of S. exigua larvae.
Figure 10B:
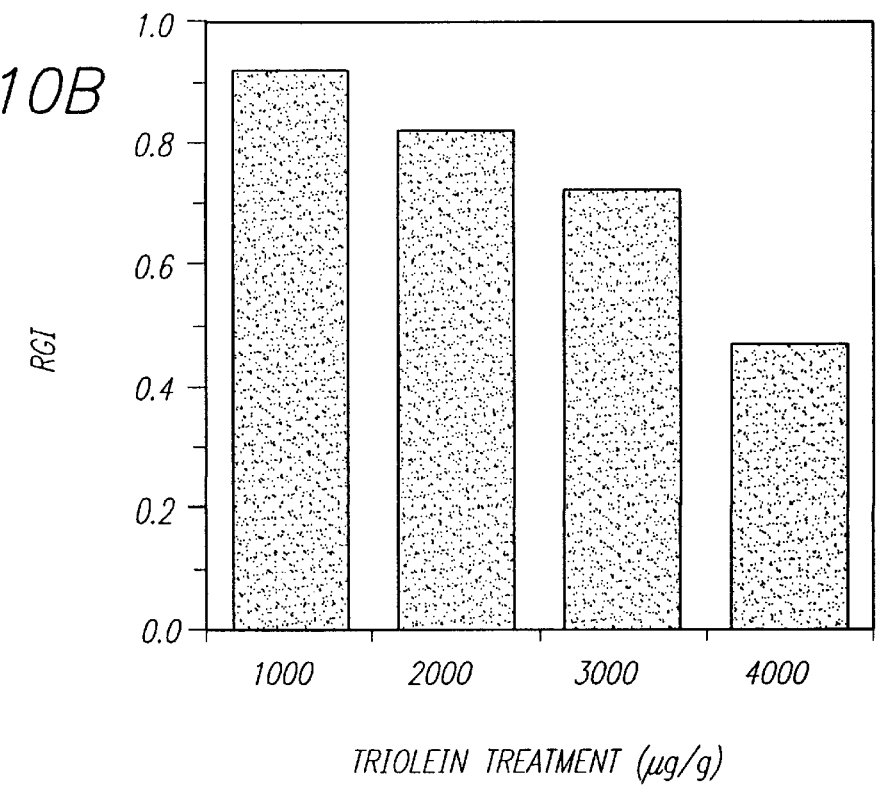

FIG. 10 are graphs showing effect of increasing concentrations of 2-(pentadecyl)furan and 2-(heptadecyl)furan (FIG. 10A) and triolein (FIG. 10B) on the relative growth index (RGI) of S. exigua larvae. Based on the values seen in FIG. 10A, toxic and inhibitory effect of both avocadofurans were comparable.

From the studies described above it is clear that both avocadofurans and triolein individually have effect on larval growth and development, that they interfere with the time needed to develop from neonate to pupa and generally that they inhibited the growth and ability of the larvae and pupae to survive. Their insecticidal activities are thus quite clearly established.

C. Synergistic Effect of Avocadofurans and Triolein Combinations

While the insecticidal activities of the avocadofurans and triolein were clearly shown, additional studies were performed to show if their individual insecticidal activity could be improved by combining them with other avocadofurans or with triolein.

Joint effects were determined by testing all combinations of $LC_{25}s$, estimated from probit lines, as seen in Table 2, of the three compounds (1), (4) and (8) for toxicity to S. exigua. The treatments were as follows: Control, 2-(pentadecyl) furan, 2-(heptadecyl)furan, triolein, individually, and 2-(pentadecyl)furan combined with 2-(heptadecyl)furan and triolein, 2-(pentadecyl)furan combined with triolein, and 2-(heptadecyl)furan combined with triolein. Because the combined $LC2_5s$ for both avocadofurans exceed their $LC_{50}$ values, a concentration for each was adjusted so that when added it would approximate the value of the avocadofurans $LC_{50}$ (see Table 2). These concentrations were used whenever both avocadofurans were combined in the same treatment. Treatments were replicated four times, with 15 larvae per replicate to a total of 60 larvae/treatment.

Combining triolein with either 2-(pentadecyl)furan or 2-(heptadecyl)furan or both resulted in a significant synergistic effect on insect mortality, as seen in Table 3. The combination of 2-(pentadecyl)furan with 2-(heptadecyl) furan did not result in synergy but in additive effect.

TABLE 2

Toxicity of 2-(pentadecyl)furan, 2-(heptadecyl)furan, and triolein to neonate S. exigua when incorporated into artificial diet

| Treatment | $N^a$ | Slope ± SE | LC25 (95% FL)$^b$ | $LC_{50}$ (95% FL)$^b$ |
| --- | --- | --- | --- | --- |
| 2-(Pentadecyl)furan | 60 | 6.523 ± 0.817 | 1.76(1.55–1.93) | 2.24(2.08–2.39) |
| 2-(Heptadecyl)furan | 60 | 2.132 ± 0.431 | 1.02(0.70–1.29) | 2.11(1.718–2.92) |
| Triolein | 60 | 2.385 ± 0.555 | 1,900(1,304–2,339) | 3,631(2,979–5,203) |

$^a$Number of insects used.
$^b$2-(Pentadecyl)furan (1) and 2-(heptadecyl)furan (4) in $\mu$moles $g^{-1}$ of diet, triolein (8) in $\mu g$ $g^{-1}$ of diet, FL = fiducial limit.

TABLE 3

Combined toxicity of 2-(pentadecyl)furan, 2-(heptadecyl)furan, and triolein against S. exigua when incorporated into artificial diet

| Mortality (%) using LC25a | | | Expected | Observed | | |
|---|---|---|---|---|---|---|
| 2-(Pentadecyl) furan | 2-(Heptadecyl) furan | Triolein | % Mortality | % Mortality | $x^2$ value | Effect[b] |
| 36.7 | 23.3 |  | 51.4 | 48.3 | 0.23 | Additive |
| 36.7 |  | 16.7 | 47.3 | 88.3 | 39.60 | Synergism |
|  | 23.3 | 16.7 | 36.1 | 90.0 | 75.56 | Synergism |
| 36.7 | 23.3 | 16.7 | 59.6 | 100.0 | 40.67 | Synergism |

[a]Actual percent mortality using estimated lethal concentration to kill 25% of S. exigua larvae.
[b]P = 0.05, df = 1

Developmental variable of S. exigua reared on diet containing combinations of avocadofurans and triolein are seen in Table 4.

TABLE 4

Developmental variables of S. exigua reared on diet containing combinations of 2-(pentadecyl)furan, 2-(heptadecyl)furan, and triolein

| Treatment | Weight (mg) | | Survival to | Developmental |
|---|---|---|---|---|
|  | 9-d larvae[a] | Pupae[b] | pupation (%) | times[c] |
| 2-(Pentadecyl)furan | 22.4 ± 2.9 a[d] | 104.3 ± 3.2 a | 63.3 | 19.8 ± 0.7 c |
| 2-(Heptadecyl)furan | 54.2 ± 5.9 b | 112.8 ± 2.6 ab | 76.6 | 18.0 ± 0.7 bc |
| Triolein | 111.8 ± 10.3 c | 116.4 ± 3.7 ab | 83.3 | 15.3 ± 0.4 ab |
| 2-(Pentadecyl)furan + 2-(heptadecyl)furan | 15.1 ± 2.7 a | 110.5 ± 3.3 a | 51.7 | 20.3 ± 0.6 c |
| 2-(Pentadecyl)furan + Triolein | 11.4 ± 5.3 a | 123.9 ± 4.4 ab | 11.7 | 18.0 ± 0.8 bc |
| 2-(Heptadecyl)furan + Triolein | 20.6 ± 8.5 a | 133.3 ± 6.9 b | 10.0 | 17.2 ± 0.9 abc |
| 2-(Pentadecyl)furan + 2-(heptadecyl)furan + Triolein | 0.0 ± 0.0 d | 0.0 ± 0.0 c | 0.0 | 0.0 ± 0.0 d |
| Control | 125.2 ± 10.2 c | 116.3 ± 3.1 ab | 95.0 | 14.6 ± 0.3 a |

[a]P = 0.001; F = 33.51; df = 6,273
[b]P = 0.015; F = 2.69; df = 6,228
[c]Neonate-pupa; P = 0.001; f = 16.31; df = 6,228
[d]Means within a column followed by the same letter are not significantly different at 5% level (Tukey Compromise Test)

Developmental data seen in Table 4 show that larvae ate at a significantly lower rate when reared on the combination of triolein with avocadofurans. These data show that the weight at day 9 were significantly reduced with combinations of furans (1) and/or (4) with triolein, and that the neonate to pupa and survival to pupation as well as developmental times were also significantly reduced.

These data clearly show that not only the avocadofurans and triolein have an insecticidal activity on their own but their combination synergistically increases this effect.

Syntheses of the above identified avocadofurans is described above and in detail in Examples 5–13.

D. Formulations

The compounds of the present invention are useful as insecticides and can be applied in a variety of ways known to those skilled in the art, at various concentrations. In practice, the compounds are applied as formulations containing the various adjuvants such as UV blockers and carriers known to or used in the industry for facilitating dispersion.

The choice of formulation and mode of application for any given compound may affect its activity, and selection will be made accordingly. The compounds of the invention may thus be formulated as adhesible micro-granules, as wettable powders, as emulsifiable concentrations, as powders or dusts, as flowables, as solutions, suspensions or emulsions, or in controlled-released forms such as microcapsules. Preferably these formulations will be used as sprays or baits. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 lb/acre, preferably from about 0.02 to about 4 lb/acre. Preferably, the dose of the furan used is between 500–1500 μg/g of plant material.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersin, or emulsifying agent.

A variety of additives and adjuvants may be incorporated into formulations containing furans of the invention. These additives and adjuvants typically change and/or enhance the physical characteristics of the carrier material and are, therefore, suitable for designing formulations having specific requirements as to the release rate and amount of the released furan, protection of the furan formulation against destruction by weather conditions, etc. These additives are, among others, plasticizers, volatility suppressants, antioxidants, lipids, various ultraviolet blockers and absorbers, spreader sticker or antimicrobials, added in amounts from about 0.001% to about 10%, preferably between 1–6%, by weight.

Antioxidants, such as vitamin E, BHA (butylated hydroxyanisole), BHT (butylated hydroxytoluene), and other antioxidants which protect the furan from degradation, are added in amounts from about 0.1% to about 3%, by weight.

Ultraviolet blockers, such as beta-carotene or p-aminobenzoic acid protect the furan from light degradation added in amounts from about 1% to about 3%, by weight.

Antimicrobials, such as potassium sorbate, nitrates, nitrites, and propylene oxide, protect the furans from microbial destruction are added in amounts from 0.1% to about 2%, by weight.

Emulsifiers, such as lecithin and modified lecithins, mono- and diglycerides, sorbitan monopalmitate, sorbitan monooleate, sorbitan monolaurate, polyoxyethylene-sorbitan monooleate, fatty acids, lipids, etc. provide or improve emulsification properties of the formulation and are added in amounts from about 1% to about 6%, by weight.

Plasticizers, such as glycerin or soy oil affect physical properties of the formulation and may extend its resistance to environmental destruction.

Emulsifiable concentrates are homogenous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extradites and relatively coarse particles, and are usually applied without dilution to the area in which suppression of insect is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which release the enclosed material at controlled rates. Encapsulated droplets are typically about 1 to 50 microns in diameter. The enclosed liquid typically constitutes about 50 to 95% of the weight of the capsules, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust, wax and granular carbon.

Other useful formulations for insecticidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely divided form as a result of vaporization of a low boiling dispersant solvent carrier, such as the Freons, may also be used.

Many of these formulations include wetting, dispersing or emulsifying agents. Examples are alkyl and alkyl-aryl sulfonates and sulfates and their salts; polyhydric alcohols; polyethoxylated alcohols; esters and fatty amines. These agents when used normally comprise from 0.5% to 15% by weight of the formulation.

The compounds of the present invention are also useful when combined with other insecticides and/or growth inhibitors, and the like. These other materials can comprise from about 5% to about 95% of the active ingredients in the formulations. These combinations frequently provide a higher level of effectiveness in controlling insects and often provide results unattainable with separate formulations of the individual insecticides.

These formulations can be applied to the areas where control is desired by conventional methods. Dust, wax dispersion and liquid compositions, for example, can be applied by the use of powerdusters, boom and hand sprayers and spray dusters. The formulations can also be applied from airplanes as a dust or a spray or by rope wick applications. The formulations can also be applied by addition to irrigation water. This permits excess distribution of the formulations onto the plants together with the irrigation water.

The following are examples of typical formulations. Active compounds in these formulations means a furan of the invention.

| Dust Formulations |
|---|
| 5% dust |
| 5 parts active compound<br>95 parts talc |
| 2% dust |
| 2 parts active compound<br>1 part highly dispersed silicic acid<br>97 parts talc. |

These dusts are formed by mixing the components then grinding the mixture to the desired particle size.

Granular Formulation

5% granules 5 parts active compound
3.5 parts polyethylene glycol
91 parts kaolin (particle size 0.3–0.8 mm)

Granules are formed by mixing the active compound with other components and dissolving the mixture in 6 parts of acetone. The polyethylene glycol is then added. The resultant solution is sprayed on the kaolin and the acetone evaporated in vacuo.

Wettable Powders

70%

70 parts active compound
5 parts sodium dibutylnahthysulfonate
3 parts naphthalenesulfonic acid/phenosulfonic acid/formaldehyde condensate (3:2:1)
10 parts kaolin
12 parts Champagne chalk.

40%

40 parts active compound
5 parts sodium lignin sulfonate
1 part sodium dibutylnaphthalenesulfonic acid
54 parts silicic acid.

25%

25 parts active compound
4.5 parts calcium lignin sulfate
1.9 parts Champagne chalk/hydroxyethyl cellulose (1:1)
1.5 parts sodium dibutylnaphthalenesulfonate
19.5 parts silicic acid
19.5 parts Champagne chalk
28.1 parts kaolin.

25%

25 parts active compound
2.5 parts isooctylphenoxy-polyethyleneethanol
1.7 parts Champagne chalk/hydroxyethyl cellulose (1:1)
8.3 parts sodium aluminum silicate
16.5 parts kieselguhr
46 parts kaolin.

10%

10 parts active compound
3 parts of a mixture of sodium salts of saturated fatty alcohol sulfates
5 parts naphthalenesulfonic acid/formaldehyde condensate
82 parts kaolin.

These wettable powders are prepared by intimately mixing the active compounds with the additives in suitable mixers, and grinding the resulting mixtures in mills or rollers.

Emulsifiable Formulation

25% Emulsifiable Concentrate 25 parts active compound
2.5 parts epoxidized vegetable oil
10 parts of an alkylarylsulfonate/fatty alcohol polyglycol ether mixture
5 parts dimethylformamide
57.5 parts xylene.

UTILITY

The compounds of this invention which are avocadofurans isolated from idioblast cells of avocado are potent, safe insecticides derived from the commonly consumed avocado fruit.

The avocadofurans are administered to lettuce, tomatoes or other crops formulated as aqueous solutions or emulsions in concentration from about 500 to about 1500 mg of insecticide per gram of plant material consumed which are effectively assuring the mortality of herbicidal insect pests, such as *S. exigua*, larvae or development of neonate larvae to pupa.

EXAMPLE 1

Extraction of Avocado Idioblast Cell

This example describes procedure used for isolation of avocado idioblast cells.

Avocado fruits (Hass) were collected from trees at the South Coast Research and Extension Center, University of California, Santa Ana, Calif. Idioblast cells were separated from ripe fruit and the oil was extracted.

Three to 5 g of mesocarp tissue was cut with a razor blade into small, 1–2 cm square pieces and placed in a Ten-Brock homogenizer with approximately 10–20 ml distilled water. The tissue was homogenized until it was completely fluid and additional water was added as necessary. The homogenate was filtered through a 200 um nylon mesh to remove vascular strands and unhomogenized groups of cells. The filtrate was saved and filtered through a 48 um nylon mesh. The residue remaining on the mesh was thoroughly washed with water, transferred to conical centrifuge tubes and centrifuged at 80 g for 2–3 minutes. The pellet was again washed and centrifuged. The washed pellet contained isolated avocado idioblast cells.

EXAMPLE 2

Tested Insects

This example describes procedure used for rearing insect used for testing of avocadofurans insecticidal activity.

*S. exigua* larvae were used in all experiments. Larvae were reared on artificial diet modified from *U.S.D.A. Agric. Res. Serv., Prod. Res. Rep.,* 1208:1 (1969), and maintained at 28+2° C., 14:10; light:dark (L:D) photoperiod.

The colony was collected from Orange Co., Calif. and had new genetic material added within 12 months prior to the study. The age of the cohorts tested was standardized by using neonates within 12 hours of eclosion. All bioassays were maintained at 28+2° C. 75% relative humidity (RH), and at 14:10 (L:D) photoperiod with fluorescent lighting.

EXAMPLE 3

Isolation and Identification of Active Compounds

This example describes procedure used for isolation and identification of active avocadofurans.

Flash chromatography was carried out using 230–400 mesh silica gel (Aldrich, Milwaukee Wis.). Electron impact (70 eV) mass spectra of volatile compounds were taken on a Hewlett-Packard 5890 GC interfaced to a 5970 mass selective detector. A DB5-MS column (30 m×0.2 mm I.D.) obtained from J&W Scientific, Folsom, Calif., was used.

Chemical ionization (methane) mass spectra were obtained with a 5890 GC (DB5 column, 30 m×0.25 mm I.D.) interfaced to an H-P 5989A mass spectrometer. Fast atom bombardment (FAB) spectra were recorded with a VG ZAB-2fHf instrument (VG Instruments, Danvers Mass.), and high resolution exact mass spectra were taken on a VG 7070E double focusing magnetic sector instrument.

$^1$H NMR spectra were recorded with a QE-300 instrument (General Electric, Fremont Calif.) in $CDCl_3$.

The crude idioblast cell oil was fractionated as shown in Scheme 1. The initial steps of the fractionation have been previously described. The lowest polarity fraction from the initial flash chromatographic separation (frac. 1, 3.67 g total weight) was further purified by flash chromatography (5 cm I.D.×25 cm), eluting sequentially with 2 liters each of toluene: ethyl ether 95:5, and 90:10 (vol:vol). The remaining material on the column was stripped off with ethanol (2 liters). Fractions were checked by thin layer chromatography (TLC) on silica plates developed with toluene: ethyl ether (90:10 vol:vol). Spots on developed plates were visualized under UV light (254 nm), followed by spraying with $H_2SO_4$ and charring with a heat gun. Subfractions were combined to yield 6 fractions (1-1 to 1-6), which were concentrated under reduced pressure, then pumped under vacuum (0.5 mm Hg) to remove traces of solvent. The concentrated fractions were weighed, then diluted with acetone to a final volume of 10 ml, and refrigerated at 4° C. until bioassayed.

A portion (75%) of the most active fraction (frac. 1-1, 1.3 g total weight) was further fractionated by flash chromatography (5 cm I.D.×25 cm), eluting sequentially with 2 liters of hexane, 1 liter of hexane: ethyl ether 95:5 (vol:vol), 0.4 liter of hexane: ethyl ether 90:10, and 0.4 liter of ethyl ether. Twelve fractions were collected, concentrated, and tested for activity. Subfractions 1-1-4 (0.08 g) compound (1), 1-1-8 (0.09 g) compound (4), and 1-1-12 (0.89 g) compound (8) contained most of the mass of material (6%, 7%, and 68%, respectively), and were most active in bioassays. Structures of identified compounds are shown in FIG. 1.

Fraction 1-1-4 contained compounds (1)–(5).

Compound (1) (39.2%). MS (70 eV): 278 (17), 249 (2), 235 (5), 221(2), 207 (2), 193 (2), 179 (3), 165 (3), 151(10), 137 (10), 123(20), 95 (57), 82 (44), 81(100). CI MS (methane): 277 (100, M−1), 279 (98, M+1), 307 (25; M+29).

Compound (2) (49.4%). MS (70 eV): 276 (25), 247 (1), 233 (1), 219 (2), 191(1), 177 (2), 163 (3), 149 (8), 135 (12), 121(9), 107 (61), 94 (100), 81(19), 79 (24), 77 (19). CI MS (methane): 275 (61, M−1), 277 (100, M+1), 305 (25, M+29).

Compound (3) (2.8%). MS (70 eV): 276(35), 247(2), 233 (2), 219(3), 191(3), 177(2), 163 (4), 149 (9), 135 (15), 121(11), 107 (60), 94 (100), 81(17), 79 (21), 77 (20). CI MS (methane): 275 (62, M−1), 277 (100, M+1), 305 (24; M+29).

Compound (4) (2.6%). MS (70 eV): 306 (28), 263 (5), 249 (4), 207 (6), 179 (3), 165 (3), 151 (13), 137 (17), 123 (35), 95 (63), 82 (54), 81(100). CI MS (methane): 305 (100, M−1), 307 (82, M+1), 335 (18, M+29).

Compound (5) (6.0%). MS (70 eV): 304(31), 247 (2), 219 (1), 193(1), 177 (3), 163 (4), 149 (11), 135 (16), 121(9), 107 (48), 95 (20), 94 (100), 81(20), 79 (20). CI MS (methane): 303 (65, M1), 305 (100, M+1), 333 (19).

$1_H$ NMR of fraction 1-1-4 ($CDCl_3$): (0.88 (ragged t, J~6.9 Hz), 1.2–1.4(m), 1.4–1.8 (m), 2.17 (m), 2.61 (t, J=7.5 Hz), 5.96 (d, J=1.4 Hz), 6.13 (d, J=1.6 Hz), 6.18 (t, J=1.8 Hz), 6.27 (distorted dd), 6.33 (distorted dd), 7.29 (m).

Fraction 1-1-8 contained compounds (6) and (7).

Compound (6) (83%). MS (70 eV): 302 (14), 273 (5), 259 (5), 245 (8), 231(7), 217 (5), 203 (3), 189 (3), 175 (3), 161(4), 149 (6), 135 (9), 121(13), 107 (12), 95 (34), 94 (36), 81(100), 67 (47), 55 (30), 41(48). HRMS: Calcd for $C_{21}H_{34}O$: 302.2610; Found: 302.2599.

1H NMR: (0.89 (3H, t, J=7.7 Hz), 1.25–1.5 (m), 1.63 (2H, m), 2.05 (4H, m), 2.61 (2H, t, J=7.6 Hz), 2.78 (2H, br. t, J=6 Hz), 5.37 (4H, m), 5.97 (1H, d, J=1.3 Hz), 6.28 (~1H, m), 7.29 (~1H, distorted d).

Compound (7) (17%).MS (70 eV):300 (32), 271 (3), 257 (3), 243 (7), 229 (20), 215 (6), 204 (5), 201 (5), 191 (9), 175 (11), 161 (9), 147 (15), 133 (21), 121 (27), 120 (31), 107 (73), 94 (100), 81 (71), 79 (86), 77 (63), 67 (52), 55 (43), 41 (65).

HRMS: Calcld for $C_{21}H_{32}O$:300.2453; Found 300.2451.

Diagnostic MS (70 eV): 300 (32), 271(3), 257 (3), 243 (7), 229 (20), 215 (6), 204 (5), (11), 161(9), 147(15), 133(21), 121(27), 120 (31), 107 (73), 94 (100), 81 67 (52), 55 (43), 41(65). HRMS: Calcd for $C_{21}H_{32}O$: 300.2453; Found:

$^1$H NMR peaks (from the spectrum of the mixed major and minor compounds): (2.18 (2H, br. quart), 6.12 (1H, m), 6.18 (1H, m), 6.34 (1H, br d). Other NMR signals for this compound were obscured under the signals from the major component of this fraction.

Fraction 1-1-12 contained solely compound (8) triolein.

Triolein was obtained by reduction of fraction 1-1-12 with $LiAlH_4$. 2 mg of the fraction was stirred with 10 mg of $LiAlH_4$ in ether (1 ml) at room temp for 2 h. The mixture was cautiously quenched with 1M aq. HCl and extracted with ether. The dried $Na_2SO_4$) extract was analyzed by GC-MS (DBS-MS column, 20 m×0.2 mm i.d., temp program 50° C./1 mm, 10° /min to 250° C.). The retention times and mass spectra of the sample components were compared with those of authentic samples of hexadecyl (palmityl) and Z9-octadecenyl (oleyl) alcohols. The mass spectrum and retention time of the third component (tentatively identified as Z9-hexadecenyl (palmitoleyl) alcohol) were compared with those of an authentic standard of Z11-hexadecenyl alcohol, providing close but not exact matches (ret. time different by 0.05 mm).

Reduction was followed with base hydrolysis.

2 mg of the fraction was dissolved in 0.5 ml EtOH, and 1 drop of 20% aq. NaOH was added. The mixture was stirred at room temp 2 h, then acidified with 1 M HCl and extracted with ether. The dried $CNa_2SO_4$ extract was analyzed by GC (DB-5, 30 m×0.32 mm i.d., temp program 50° C./1 mm, 15° /min to 275° C.), and the retention times of the sample components were compared with those of authentic standards of oleic, palmitic, and palmitoleic acids.

1H N MR ($CDCl_3$): (0.88 (9H, distorted t), 1.2–1.4 (m), 1.61 (~6H, m), 2.02 (12H, m), 2.32 (6H, distorted t, J 7.4 Hz), 4.15 (2H, dd, J=11.9, 6 Hz), 4.30 (2H, dd, J=11.9, 4 Hz), 5.27 (1H, m), 5.33 (6H, m). FAB-MS (nitroberiz~1 alcohol matrix): Highest mass peak cluster centered at m/z 603 (M-$C_{18}H_{35}O_2$).

EXAMPLE 4

Bioassays

This example describes conditions used in bioassays for testing of compounds described in Section I and FIGS. 1–4.

The insecticidal activity of the fractions was tested with artificial diet bioassays. Treated diets were prepared by transferring 750 μl of acetone solutions of each fraction (equivalent to 300 mg crude idioblast cell oil) into 50-ml polypropylene centrifuge tubes (Fisher, Pittsburgh Pa.), evaporating the acetone, adding 2 ml of 0.1% Tween-80 solution (Fisher), homogenizing with an ultrasonic homogenizer (Co le-Parmer, Chicago Ill.), and adding prepared diet to produce a final weight of 15 g containing the equivalent of 2% idioblast oil. The mixture was vortexed for 3 mm.

Control diet was prepared by mixing 2 ml of Tween solution and 13 g of artificial diet to produce a final weight of 15 g. Control and treated diets were poured into 24-well (15.9 mm diameter and 15.9 mm depth) bioassay trays (C-D International Inc., Pitman N.J.). One neonate was added per well, and trays were placed in an incubator under the previously described conditions. Twenty-four neonates were tested for each fraction and control. Mortality and larval weights were recorded after 7 days.

EXAMPLE 5

Synthesis of Furan Compounds

Reactions were carried out under $N_2$ atmosphere unless otherwise stated. Flash chromatography was carried out with 230–400 mesh silica gel. THF was dried by distillation from sodium-benzophenone ketyl. 'H-NMR spectra were obtained on a 270 MHZ JOEL NMR spectrometer, in $CDCl_3$ or $C_6D_6$. $^{13}C$-NMR spectra were obtained at 67.9 MHZ in CDCl3. Infrared spectra were obtained on a Mattson Galaxy 2000 FT-IR using NaCl plates, or in carbon tetrachloride solution. Mass spectra (HRMS and LRMS) were obtained from the University of California Riverside, Mass Spectroscopy Laboratory.

EXAMPLE 6

Preparation of 2-(pentadecyl)furan

This example describes the preparation of 2-(pentadecyl)furan compound(1) according to Scheme 2A.

A dry 50 ml round bottom flask charged with furan (1.40 g, 20.6 mmol) and THF (10 ml), was cooled to −78° C. and n-butyllithium (13.6 ml, 1.50 M in hexanes, 20.6 mmol) was added dropwise. The solution was stirred for 30 mm at −78° C., then warmed to 0° C. and placed in an ice bath for 1 h. The mixture was then cooled to −78° C. and 1-bromopentadecane 9 (5 g, 17.2 mmol) in THF (10 ml) were added dropwise. The resulting solution was stirred for 1 h, then warmed to room temp and stirred 12 h. The reaction was quenched with a saturated solution of NH4Cl (5 ml). The organic layer was separated and the aqueous layer extracted with ether (3×20 ml). The combined organic layers were washed with saturated $NaHCO_3$ (1×20 ml), brine (1×20 ml), dried over $MgSO_4$, filtered and concentrated under vacuum. The crude product was purified by flash chromatography on silica, eluting with hexanes to afford a oily liquid that was recrystallized from methanol (~50 ml/g, cooling to 5° C.) to afford 4.8 g (64%) of 2-(pentadecyl)furan (1).

$^1H$ NMR: ($CDCl_3$) (0.85) 3H, distorted t, J~7.2 Hz), 1.1–1.4 (24H, broad m), 1.57 (2H, quintet, J~7.2 Hz), 2.58 (2H, t, J 7.2 Liz), 5.99 (1H, dd, J~1, 3.0 Hz), 6.29 (1H, dd, J~1.8, 3.0 Hz), 7.29 (1H, dd, J~1, 1.8 Hz).

EXAMPLE 7

Preparation of 2-(7-heptadecyl)furan

This example describes preparation of 2-(7-heptadecyl)furan, compound(4).

1-Heptadecanol (10 g, 39.1 mmol) was placed in a dry 25 ml round bottom flask attached to a reflux condenser and heated to 60° C. under a nitrogen atmosphere. Phosphorous tribromide (10 g, 39.1 mmol) was added dropwise and the resulting solution was stirred for 48 h. The reaction mixture was then cooled in an ice bath and quenched with a saturated solution of $NaHCO_3$ (10 ml). The aqueous layer was extracted with ether (4×10 ml). The combined organic layers were dried over $MgSO_4$, filtered and concentrated. The crude residue was flash chromatographed (hexanes) to afford 7.2 g (57%) of 1-bromoheptadecane as a colorless oil.

$^1$H-NMR ($CDCl_3$): (0.85 (3H, t, J~6.5 Hz), 1.1–1.4 (28H, broad s), 1.86 (2H, quintet, J~6.8 Hz), 3.41 (2H, t, J 6.8 Hz).

2-(heptadecyl)furan (4) was prepared exactly as described above for 2-(pentadecyl)furan, substituting 1-bromo heptadecane for 1-bromopentadecane. The chromatographed product was recrystallized from methanol as described above to afford of 2-(heptadecyl)furan (4) in 48% yield.

1H-NMR (CDCl3): (0.86 (3H, distorted t, J~7.2 Hz), 1.1–1.4 (28H, broad m), 1.60 (2H, quintet, J~7.2 Hz), 2.58 (2H, t, J 7.2 Hz), 5.95 (1H, dd, J~1.0, 2.7 Hz), 6.26 (1H, J~1.8, 2.7 Hz), 7.30 (1H, dd, J~1.0, 1.8 Hz).

EXAMPLE 8

Preparation of 2-(1Z-pentadecyl)furan

This example describes preparation of 2-(1Z-pentadecyl)furan, compound (3), according to Scheme 2B.

A mixture of 1-bromotetradecane (10) (10.0 g, 36.1 mmol), triphenylphosphine (10.5 g, 36.1 mmol) and benzene (25 ml) was refluxed for 48 h, then the mixture was concentrated under reduced pressure to a viscous oil. Addition of ether afforded a white solid, which was dried under vacuum for 24 h at 65° C., yielding 18.9 g (92%) of tetradecyltriphenylphosphonium bromide 11, which was used without further purification.

Potassium hydride (2.33 g, 20.2 mmol, 35% oil dispersion) was washed with hexanes (3×5 ml) and pumped under vacuum. After 5 mm, the flask was filled with $N_2$, dry THF (50 ml) was added and the reaction flask cooled in an ice bath. The phosphonium salt 11 (10 g, 18.5 mmol) was added in small portions over a 20 mm period. After stirring for 15 mm, the resulting yellow solution was warmed to room temperature and stirred for 30 mm, then cooled to −78° C.

Freshly distilled furaldehyde (2.1 g, 22.2 mmol) in THF (25 ml) was added dropwise over 15 min. The resulting solution was stirred for 1 h, then warmed to room temperature and stirred for 18 h. The reaction was quenched with saturated aq. $NH_4Cl$ (50 ml). The organic layer was separated and the aqueous layer was extracted with ether (3×20 ml). The combined organic layers were washed with saturated $NaHCO_3$ (1×25 ml) and brine (1×25 ml), dried over $MgSO_4$, filtered, and concentrated under vacuum. The crude product was purified by flash chromatography (hexanes), to afford 4.2 g (81%) of a mixture of furans 3 and 2 (7:3 cis/trans ratio).

$^1$H-NMR of major product: ($CDCl_3$) (0.92 (3H, distorted t, J~7.0 Hz), 1.2–1.6 (22H, m), 2.45 (2H, apparent dq, J~1.8 Hz, 7.1 Hz), 5.58 (1H, dt, J 11.6, 7.1 Hz), 6.2–6.3 (2H, m), 6.40 (1H, dd, J~3.2, 2.0 Hz), 7.38 (1H, d, J 1.7 Hz).

EXAMPLE 9

Preparation of 2-(]E-pentadecenyl)furan

This example describes preparation of 2-(]E-pentadecenyl)furan compound (2) according to Scheme 2B.

The diastereomeric mixture of 2-(1-pentadecenyl)furan 2 and (3) (1.0 g, 3.4 mmol) was placed in a stirred 2% iodine/benzene solution (10 ml) in an open beaker and irradiated with a fluorescent light. The cis- to trans-isomerization was monitored by NMR (scanned unlocked, observing the disappearance of the resonance at (=5.58 (1H, dt, J 11.9 Hz, 6.9 Hz, cis-isomer) and appearance of the resonance at (=6.3 (1H, dt, J 16.1 Hz, 6.9 Hz, trans-isomer). After 30 mm of irradiation, the reaction mixture was washed thoroughly with saturated sodium thiosulfate. The organic layer was separated, dried over $MgSO_4$, filtered and concentrated. The crude product was passed through a silica gel plug (hexanes). The eluate was concentrated and the oily residue was recrystallized from methanol as described above, filtering cold to afford 0.53 g (57%) of compound (2) as low-melting white crystals.

$^1$H NMR ($C_6D_6$): (0.90 (3H, distorted t, J~7.0 Hz), 1.2–1.5 (22H, m), 2.05 (2H, apparent q, J 6.9 Hz), 5.95 (1H, d, J 3. Hz), 6.16 (1H, m), 6.20 (1H, d, J 16.1 Hz), 6.30 (1H, dt, J~16.1 Hz, 6.9 Hz), 7.06 (1~I, s).

EXAMPLE 10

Preparation of 2-(8Z,11Z-heptadecadienyl)furan

This example describes preparation of 2-(8Z,11Z-heptadecadienyl)furan compound (6), according to Scheme 3 includes preparation of compounds (13), (14), (15) and (16).

Preparation of 9,10,12,13-Tetrabromooctadecanoic Acid compound(13).

Bromine (10.6 g, 66.6 mmol) was added dropwise to a rapidly stirred solution of linoleic acid (12) (8.9 g, 31.7 mmol) in diethyl ether (264 ml) at 0° C. After stirring for 30 mm, the solution was warmed to room temperature and quenched by addition of saturated aq. sodium thio sulfate (20 ml). After stirring for 10 mm, the organic layer was separated and the aqueous layer extracted with ether (3×20 ml). The combined organic layers were washed with saturated aq. $NH_4Cl$ (2×10 ml) and brine (1×10 ml), dried over $MgSO_4$, filtered and concentrated. The crude product was recrystallized for pentane/ether (1:1) to afford 16.6 g (85%) of the tetrabromo acid (13) as white crystals.

$^1$H NMR ($CDCl_3$): (0.89 (3H, distorted t, J~6.3 Hz), 1.1–2.1 (18H, m), 1.60 (2H, m), 1.83 (2H, m), 2.01 (2H, m), 2.34 (2H, t, J 7 Hz), 2.48 (2H, m).

Preparation of 1,8,9,11,12-Pentabromoheptadecane, compound (14).

A 500 ml round bottom flask, equipped with a reflux condenser and addition funnel, was charged with tetrabromo acid (13) (16.4 g, 27.3 mmol), carbon tetrachloride (135 ml) and mercuric oxide (8.87 g, 41.0 mmol) and brought to a gentle reflux. Bromine (3.1 g, 41 mmol) was added dropwise over 30 mm. After refluxing 2 h, the reaction was cooled to room temp and quenched with a 10% solution of sodium thiosulfate (50 ml). The organic layer was removed and the aqueous layer was extracted with carbon tetrachloride (2x~20 ml). The combined organic layers were washed with saturated ag. $NH_4Cl$ (2×20 ml) and brine (1×20 ml), dried over $MgSO_4$, filtered and concentrated. The crude product was purified by flash chromatography (hexanes) and recrystallized (pentane) at 5° C. to afford 10.9 g (63%) of pentabromide 14 as white crystals (m.p. 62–64° C.).

$^1$H NMR ($CDCl_3$): (0.88 (3H, distorted t, J~6.5 Hz) 1.1–2.1 (18H, m), 2.50 (2H, m), 3.34 (2H, t, J 7.3 Hz), 4.0–4.2 (211, m), 4.32 (2H, m), 4.54 (2H, m).

Preparation of (8Z,11Z) -1-Bromoheptadecadiene compound (15).

Pentabromide (14) (5.35 g, 8.42 mmol and zinc powder (1.2 g, 18.5 mmol) in THF (55 ml) were refluxed 4 h. The reaction mixture was then cooled to room temperature and concentrated under reduced pressure. The oily residue was extracted into ether/pentane (1:1), the solution was concentrated and the crude product was purified by flash chromatography (pentanes) to afford 2.6 g (>95%) of the (Z,11-diene 15 as a colorless oil.

$^1$H NMR ($CDCl_3$): (0.87 (3H, distorted t, J~6.9 Hz), 1.2–1.4 (14H, m), 1.82 (2H, quintet, J~6.9 Hz), 2.03 (411, apparent q, J 6.8 Hz), 2.75 (2H, t, J 5.9 Hz), 3.38 (211, t, J 7 Hz), 5.2–5.5 (4H, m).

Preparation of (8Z,11Z)-1-iodoheptadecadiene compound (16).

(Z,Z)-Bromodiene 15 (2.67 g, 8.45 mmol) and sodium iodide (3.80 g, 25.3 mmol) in acetone (133 ml) were refluxed 4 h. The reaction mixture was then cooled to room temperature, filtered, concentrated and extracted with ether (3×20 ml). The ether extracts were filtered and concentrated and the residue purified by flash chromatography (0.87 (3H, (pentane) to afford 2.25 g (74%) of the (ZZ),-iododiene (16).

$^1$H NMR ($CDCl_3$): distorted t, J~6.9 Hz), 1.2–1.4 (14H, m), 1.79 (211, quintet, J~6.9 Hz), 2.03 (4H, apparent q, J 6.9 Hz), 2.76 (2H, t, J 5.9 Hz), 3.17 (2H, t, J 7 Hz), 5.2–5.5 (411, m).

Preparation of 2-(8Z,11Z-heptadecadienyl)furan compound 6.

Furan (1.1 g, 16.1 mmol) in THF (5 ml) was cooled to −78° C. and n-butyllithium (5.4 ml, 1.5 M in hexanes, 8.1 mmol) was added dropwise. The resulting solution was stirred 30 mm at −78° C., warmed to 0° C. for 1 h, then recooled to −78° C. (Z,Z-Iododiene (16) (2.94 g, 8.1 mmol) in THF (5 ml) was added via cannula, and the mixture was stirred 2 h. The reaction was then warmed to room temperature and stirred an additional 2 h, then quenched with saturated aq. $NH_4Cl$ (10 ml). The aqueous layer was separated and extracted with ether (3×10 ml). The combined organic layers were washed with saturated $NaHCO_3$ (2×10 ml) and brine (1×10 ml), dried over $MgSO_4$, filtered and concentrated. The crude residue was passed through a silica gel plug (hexane), then purified by HPLC (Rainin Dynamax column, 2.24×25 cm, Rainin Instruments, Emeryville Calif.) eluting with hexanes, to afford 1.0 g (41%) of furanyl diene compound (6) as a colorless oil.

$^1$H N\ilR ($CDCl_3$): (0.87 (311, distorted t, J~7.0 Hz), 1.2–1.4 (14H, m), 1.66 (2H, quintet, J~6.6 Hz), 2.08 (4H, apparent q, J 6.4 Hz), 2.64 (2H, t, J 7.4 Hz), 2.80 (211, t, J 5.6 Hz), 5.2–5.5 (4H, m), 5.99 (1H, m), 6.28 (1H, m), 7.30 (1H, m).

EXAMPLE 11

Preparation of 2-(Tetradecyl)furan

This example describes preparation of 2-(tetradecyl)furan compound (20).

Into a dry 25 mL round bottom flask was placed THF (4 mL) and cooled under nitrogen to −20° C. Furan (1.05 mL, 0.98 g, 14.4 mmol) was added to the flask and allowed to cool for 5 mm. N-BuLi (6.00 mL, 9.00 mmol 1.5 M in hexanes) was added dropwise and the resulting solution stirred for 1 h, warmed to room temperature for 15 mm then recooled to −20° C.

1-Bromotetradecane (2.05 g, 8.17 mmol) in THF (4 mL) was added dropwise and the resulting solution was warmed to room temperature and stirred overnight. The reaction was quenched with a saturated solution of NH$_4$Cl (5 mL). The organic layer was removed and the aqueous layer extracted with ether (3×5 mL). The combined organic layers were washed with a saturated solution of NaHCO$_3$ (1×5 mL), brine (1×5 mL), dried over MgSO$_4$, filtered and concentrated. The crude residue was passed through a small silica gel plug and recrystallized in methanol to afford the 2-(tetradecyl)furan, compound (20) (1.50 g, 77% yield).

$^1$H-NMR; 270 MHZ: (CDCl$_3$) δ=0.89 (3H, —CH$_3$, distorted triplet, J 6.6 Hz) 1.26 (22 H, —CH$_2$—, br s,), 1.63 (2H, H$_2$, quintet, J 7.2 Hz) 2.60 (2H, H$_1$, t, J 7.4 Hz), 5.96 (1H, Ar—H, m), 6.26, (1H, Ar—H, m), 7.27 (1H, Ar—H, m).

$^{13}$C-NMR 67.5 MHZ (CDCl$_3$) δ=14.00, 22.79, 28.07, 28.14, 29.30, 29.47, 29.75, 29.76, 29.78, 29.80, 104.55, 110.07, 140.65, 156.70. IR: CCl$_4$, KBr, 2860(s), 2790(s), 1580(m), 1440(s), 1130(m), 990(m), 700(s) cm$^{-1}$.

EXAMPLE 12

Preparation of 2-(Hexadecyl)furan

This example describes preparation of 2-(hexadecyl)furan compound (21).

Into a dry 25 mL round bottom flask was placed THF (4 mL) and cooled under nitrogen to −20° C. Furan (1.08 mL, 1.01 g, 14.8 mmol) was added to the flask and allowed to cool for 5 mm. N-BuLi (5.3 mL, 7.90 mmol, 1.5 M in hexanes) was added dropwise and the resulting solution stirred for 1 h, warmed to room temperature for 15 mm, then recooled to −20° C.

1-Bromotetradecane (2.0 g, 6.58 mmol) in THF (4 mL) was added dropwise and the resulting solution was warmed to room temperature and stirred overnight. The reaction was quenched with a saturated solution of NH$_4$Cl (5 mL). The organic layer was removed and the aqueous layer extracted with ether (3×5 mL). The combined organic layers were washed with a saturated solution of NaHCO$_3$ (1×5 mL), brine (1×5 mL), dried over MgSO$_4$, filtered and concentrated. The crude residue was passed through a small silica gel plug and recrystallized in methanol to afford the 2-(hexadecyl)furan compound (21) (1.45 g, 76% yield).

$^1$H-NMR; 270 MHZ: (CDCl$_3$) δ=0.88 (3H, —CH$_3$, distorted triplet, J 6.7 Hz) 1.26(26 H, —CH$_2$—, brs,), 1.63 (2H, H$_2$, quintet, J 7.2 Hz) 2.60 (2H, H$_1$, t, J 7.4 Hz), 5.96 (1 H, Ar—H, m), 6.26, (1H, Ar—H, m), 7.27 (1H, Ar—H, m).

$^{13}$C-NMR 67.5 MHZ (CDCl$_3$)δ=14.00, 22.79, 28.06, 28.13, 29.29, 29.46, 29.65, 29.73, 29.77, 29.79, 104.55, 110.06, 140.65, 156.70. IR, CCl$_4$, KBr, 2860(s), 2790(s), 1580(m), 1430 (s), 1125 (m), 980 (m), 700 (s) cm$^{-1}$.

EXAMPLE 13

Preparation of 2-(Octadecyl)furan

This example describes preparation of 2-(octadecyl)furan compound (22).

Into a dry 25 mL round bottom flask was placed THF (4 mL) and cooled under nitrogen to −20° C. Furan (1.05 mL, 0.98 g, 14.4 mmol) was added to the flask and allowed to cool for 5 mm. N-BuLi (7.2 mL, 10.8 mmol, 1.5 M in hexanes) was added dropwise and the resulting solution stirred for 1 h, warmed to room temperature for 15 mm, then recooled to −20° C.

1-Bromotetradecane (3.0 g, 9.01 mmol) in THF (4 mL) was added dropwise and the resulting solution was warmed to room temperature and stirred overnight. The reaction was quenched with a saturated solution of NH$_4$Cl (5 mL). The organic layer was removed and the aqueous layer extracted with ether (3×5 mL). The combined organic layers were washed with a saturated solution of NaHCO$_3$ (1×5 mL), brine (1×5 mL), dried over MgSO$_4$, filtered and concentrated. The crude residue was passed through a small silica gel plug and recrystallized in methanol to afford the 2-(octadecyl)furan compound (22) (2.61 g, 90% yield).

$^1$H-NMR; 270 MHZ: (CDCl$_3$) δ=0.85 (3H, —CH$_3$, distorted triplet, J 6.7 Hz) 1.23 (28 H, —CH$_2$—, br s,), 1.6 (2H, H$_2$, quintet, J 7.2 Hz) 2.60 (2H, H$_1$, t, J 7.4 Hz), 5.95 (1H, Ar—H, m), 6.26, (1H, Ar—H, m), 7.27 (1H, Ar—H, m).

$^{13}$C-NMR 67.5 MHZ (CDCl$_3$) δ=14.19, 22.77, 28.06, 28.11, 29.26, 29.44, 29.63, 29.77, 32.00, 104.55, 110.07, 140.65, 156.71. IR: CCl$_4$, KBr, 2926(s), 2856(m), 1461(w), 1147(w), 1007(w), 732(w) cm$^1$.

EXAMPLE 14

Toxicity Studies

This example describes studies for determination of toxicity of avocadofurans.

The effect of the synthetically produced avocado furan compounds (>95% purity) and commercially available triolein (Sigma, St. Louis, Mo.) were tested on larval growth and mortality of S. exigua. Treated and control diet were prepared as previously described.

Data described above showed that of the two compounds identified from subfraction 1-1-4, 2-(1E-pentadecenyl)furan (2) had little effect on survivorship and growth of S. exigua compared to its saturated analog, 2-(pentadecyl)furan (1). Similarly, 2-(8Z,11Z-heptadecadienyl)furan (6) was of much lower toxicity than 2-(heptadecyl)furan (4). Consequently, the two saturated compounds were selected for this study.

Six different compound concentrations, chosen on the basis of studies with the oil fractions, were evaluated for both 2-(pentadecyl)furan and 2-(heptadecyl)furan: 0 (control), 600, 750, 900, 1050, and 1200 μg/g. Also, six concentrations of triolein (subfraction 1-1-12) were tested: 0 (control), 7000, 8000, 9000, 10000, and 11000 μg/g.

Twenty-four neonates were used per treatment. Bioassays were conducted as described in Example 4, and replicated 4 times for each concentration (i.e., a total of 96 larvae were tested for each concentration). Larval weight, instar, and mortality were recorded after 7 days at day 9.

EXAMPLE 15

Toxicity of Furan Analogs and Avocadofurans

This example describes procedures used for testing of toxicity of avocadofurans and furan analogs.

Five saturated furans of variable side chain lengths: 2-(tetradecyl)furan (20), 2-(pentadecyl)furan (1), 2-(hexadecyl)furan (21), 2-(heptadecyl)furan (4), and 2-(octadecyl)furan (22) were tested for activity against S. exigua in diet bioassays. Treated diets were prepared at a concentration known to be insecticidal against S. exigua early instars (5 μmoles g$^{-1}$ diet). To compare toxicity among furans, concentrations in μmoles g$^{-1}$ of diet were used to compensate for their different molecular weights.

This example describes conditions used in bioassays for testing of compounds described in Section I and FIGS. 1–4. Each furan compound was transferred into a 50-ml polypropylene centrifuge tube (Fisher, Pittsburgh Pa.), added 2 ml of 0.1% Tween-80 solution (Fisher), homogenized with an ultrasonic homogenizer (Cole-Parmer, Chicago, Ill.), and artificial diet was added to produce a final weight of 15 g. The mixture was vortexed for 3 mm. Control diet was prepared by mixing 2 ml of Tween solution with 13 g of artificial diet to produce a final weight of 15 g. Control and treated diets were poured into 16-well bioassay trays (C-D International Inc., Pitman N.J.). One neonate was added per well. Trays were placed in an incubator set for conditions described previously. Twenty-four neonates were tested for each treatment. Each treatment was replicated four times (total of 96 larvae/treatment). Larval mortality and weight were recorded after 9 days.

EXAMPLE 16

Individual Toxicity of Avocadofurans

This example describes procedures used for testing of individual toxicity of avocadofurans and triolein.

Two of the most toxic furans, 2-(pentadecyl)furan and 2-(heptadecyl)furan, were examined. Following pilot studies, eight concentrations of each were tested: 0, 0.5, 1, 1.5, 2, 2.5, 3, and 3.5 $\mu$moles $g^{-1}$ diet. Also, five concentrations of triolein were tested: 0; 1,000; 2,000; 3,000; and 4,000 $\mu$g $g^{-1}$ diet. Because triolein was not compared to a structurally similar compound, a more standard dietary formulation of $\mu$g $g^{-1}$ was used rather than ~moles $g^{-1}$ in all triolein-treated bioassays.

Treated and control diet were prepared as described above. For each concentration the compounds were dissolved in 10 ml of Tween solution and mixed using an ultrasonic homogenizer. Untreated diet was added to make a total of 100 g and then vortexed for 3 mm. Control diet was prepared by mixing 10 ml of the Tween solution with 90 g of artificial diet to produce a final weight of 100 g. Control and treated diets were poured into 30 ml plastic cups. One neonate was placed in each cup and cups were held in an incubator. Fifteen larvae were tested at each concentration, and assays were replicated 4 times (total of 60 larvae/treatment). For each diet treatment, 9-d larval instar and weight, pupal weights, times to pupation, and larval mortality were recorded.

EXAMPLE 17

Toxicity Synergism of Avocadofurans and Triolein Combinations

This example illustrates studies performed for determination of toxicity synergism of avocadofurans and triolein.

Joint effects were determined by testing all combinations of $LC_{25}$s (estimated from probit lines shown in Table 1) of the three compounds for toxicity to S. exigua. The treatments were: control, 2-(pentadecyl)furan, 2-(heptadecyl)furan, triolein, 2-(pentadecyl)furan+triolein, 2-(heptadecyl)furan+triolein, and 2-(pentadecyl)furan+2-(heptadecyl)furan+triolein. Because the combined $LC_{25}$s for both avocadofurans exceeded their $LC_{50}$ values (due to a steep slope of their LC lines), a concentration for each was used so that when added together it would approximate the value of the avocadofurans $LC_{50}$ (Table 1). These concentrations were used whenever both avocadofurans were combined in the same treatment.

Treatments were replicated four times, with 15 larvae per replicate (total of 60 larvae/treatment). Dietary treatment preparations and bioassay procedures were conducted as described in Example 4. For each diet treatment, 9-d larval instar and weight, pupal weights, times to pupation, and larval mortality were recorded.

EXAMPLE 18

Statistical Data Analysis

This example describes methods used for data and statistical analysis and interpretation of results.

EC (effective concentration) values were calculated by subtracting the mean larval weight for each treatment from the mean weight of the controls, and dividing by the mean weight of the controls. LC (lethal concentration) values were obtained using probit analysis as described in *Probit Analysis* (1971) Cambridge University Press, Cambridge, UK. GI (growth index) and RGI (relative growth index) values were calculated as described in *J. Chem. Ecol.*, 19:1109 (1993), but using an $i_{max}$ of 3 (the stage attained by most control larvae after 7 d). Statistical comparisons were conducted using SuperAnova Abacus Concept Inc., Berkeley, Calif. (1989).

What is claimed:

1. An insecticidal composition comprising an insecticidally effective amount from about 5% to about 95%, by weight, of a compound selected from the group of compounds consisting of 2-(tetradecyl)furan, 2-(pentadecyl)furan, 2-(hexadecyl)furan, 2-(heptadecyl)furan, 2-(octadecyl)furan, 2-(1E-pentadecenyl)furan, 2-(1Z-pentadecenyl)furan, 2-(8Z, 11Z-heptadecadienyl)furan and a mixture thereof isolated from idioblast oil cells of avocado or synthetically prepared, wherein said compound or a mixture thereof inhibits insect growth or larval development.

2. The composition of claim 1 further comprising triolein.

3. The composition of claim 1 wherein the compound is 2-(heptadecyl)furan present in concentration from 0.1 to about 3.5 $\mu$moles per $g^{-1}$ of the composition.

4. The composition of claim 1 wherein the compound is 2-(pentadecyl)furan present in concentration from 0.1 to about 3.5 $\mu$moles per $g^{-1}$ of the composition.

5. The composition of claim 1 comprising a mixture of 2-(heptadecyl)furan and 2-(pentadecyl)furan each present in concentration from 0.1 to about 3.5 $\mu$moles per $g^{-1}$ of composition.

6. The composition of claim 3 in admixture with triolein present in concentration from about 1 to about 5000 $\mu$g $g^{-1}$ of the composition.

7. The composite of claim 4 in admixture with triolein present in concentration from about 1 to about 5000 $\mu$g $g^{-1}$ of the composition.

8. The composition of claim 5 in admixture with triolein present in concentration from about 1 to about 5000 $\mu$g $g^{-1}$ of the composition.

9. The composition of claim 2 formulated as adhesible micro-granules, wettable powder, dust, flowables, solution, suspension, emulsion, or microcapsules.

10. An insecticidal composition comprising a mixture of 2-(heptadecyl)furan and 2-(pentadecyl)furan.

11. An insecticidal composition comprising 2-(pentadecyl)furan in admixture with triolein.

12. The composition of claim 10 in admixture with triolein.

13. An insecticidal composition for control of insects' growth and larval development comprising an insecticidally effective amount of a compound selected from the group consisting of 2-(tetradecyl)furan, 2-(pentadecyl)furan, 2-(heptadecyl)furan, 2-(octadecyl)furan, 2-(octadecyl)furan, 2-(1E-pentadecenyl)furan, 2-(1Z-pentadecenyl)furan, 2-(8Z, 11Z-heptadecadienyl)furan, and a mixture thereof in admixture with an additive or adjuvant wherein the additive is an antioxidant, an ultraviolet blocker, an antimicrobial or emulsifier.

14. A method for controlling insects by inhibiting the insect's growth and larval development said method comprising a step of applying to the area where control is desired, an insecticidally effective amount of a composition comprising a compound selected from the group consisting of 2-(tetradecyl)furan, 2-(pentadecyl)furan, 2-(hexadecyl)furan, 2-(heptadecyl)furan, 2-(octadecyl)furan, 2-(1E-pentadecenyl)furan, 2-(1Z-pentadecenyl)furan, 2-(8Z, 11Z-heptadecadienyl)furan, and a mixture thereof isolated from idioblast oil cells of avocado or synthetically prepared, said compound present in the composition in concentration from about 5% to about 95%.

15. The method of claim 14 wherein said composition comprises 2-(heptadecyl)furan present in concentration from 0.1 to 3.5 $\mu$moles per $g^{-1}$ of the composition.

16. The method of claim 14 wherein said composition comprises 2-(pentadecyl)furan present in concentration from 0.1 to 3.5 $\mu$moles per $g^{-1}$ of the composition.

17. The method of claim 15 wherein the composition additionally comprises triolein.

18. The method of claim 14 wherein said composition further comprises an antioxidant, ultraviolet blocker, an antimicrobial or emulsifier.

19. The method of claim 15 wherein the composition further comprises 2-(pentadecyl)furan.

20. The method of claim 14 comprising applying said composition to the area where insect control is desired at a rate from about 0.01 to about 10 lb per acre.

21. The method of claim 19 wherein the 2-(heptadecyl)furan and 2-(pentadecyl)furan are in admixture with triolein.

* * * * *

UNITED STATES PATENT AND TRADEMARK OFFICE
Certificate

Patent No. 6,133,313

Patented: October 17, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William W. Thomson, Riverside, CA; Kathryn A. Platt, Riverside, CA; John T. Trumble, Riverside, CA; Cesar Rodriguez-Saona, Lima, Peru; and Jocelyn Millar, Riverside, CA.

Signed and Sealed this Eighteenth Day of October 2005.

CECILIA J. TSANG
*Supervisory Patent Examiner*
Art Unit 1600